(12) United States Patent
Jackson et al.

(10) Patent No.: US 10,449,310 B2
(45) Date of Patent: Oct. 22, 2019

(54) SECURITY FEATURES FOR AN ELECTRONIC METERED-DOSE INHALER SYSTEM

(71) Applicant: Optimist Inhaler LLC, Buford, GA (US)

(72) Inventors: David N Jackson, Buford, GA (US); Russell M Smith, Buford, GA (US)

(73) Assignee: Optimist Inhaler LLC, Gainesville, GA (US)

( * ) Notice: Subject to any disclaimer, the term of this patent is extended or adjusted under 35 U.S.C. 154(b) by 0 days.

(21) Appl. No.: 16/270,375

(22) Filed: Feb. 7, 2019

(65) Prior Publication Data

US 2019/0240430 A1    Aug. 8, 2019

Related U.S. Application Data

(60) Provisional application No. 62/628,102, filed on Feb. 8, 2018, provisional application No. 62/644,837, filed on Mar. 19, 2018.

(51) Int. Cl.
*A61M 15/00* (2006.01)
*A61B 5/00* (2006.01)
*G16H 10/60* (2018.01)

(52) U.S. Cl.
CPC ...... *A61M 15/0081* (2014.02); *A61M 15/008* (2014.02); *A61M 15/009* (2013.01);
(Continued)

(58) Field of Classification Search
CPC .............. A61M 15/00; A61M 15/0021; A61M 15/0065; A61M 15/0068; A61M 15/007;
(Continued)

(56) References Cited

U.S. PATENT DOCUMENTS

| 5,392,768 A | 2/1995 | Johansson et al. |
| 5,507,277 A * | 4/1996 | Rubsamen ............ A61M 15/00 128/200.14 |

(Continued)

FOREIGN PATENT DOCUMENTS

| CA | 2822738 A1 | 6/2012 |
| EP | 1388115 A2 | 3/2004 |

(Continued)

OTHER PUBLICATIONS

Kira, 3D printed smart inhaler could help doctors better understand asthma, Mar. 14, 2016.

(Continued)

*Primary Examiner* — Colin W Stuart
(74) *Attorney, Agent, or Firm* — Mehrman Law Office; Michael J. Mehrman

(57) ABSTRACT

Security features for an electronic metered-dose smart inhaler, mobile app, and cloud-based software system that validates users and inhaler use protocols, such as medical prescriptions and clinical trial regimens. The smart inhaler interacts with a mobile app to control and monitor per-dose usage and capture efficacy results and feedback from medical patients and clinical trial participants for review by prescribing physicians, clinical trial administrators, medicine formulators and artificial intelligence. While the smart inhaler system is well suited for aerosol medical marijuana products, it may be used to deliver and conduct clinical trials on any type of product suitable for aerosol administration including other types of medication and non-medical products, such as nicotine, herbal products, pain killers, sleep aids, dietary stimulants, dietary suppressants, etc. Many of the system-based innovations are not limited to aerosol inhalers, and may be applied more widely to other types of in-home, patient-administered products.

20 Claims, 18 Drawing Sheets

(52) U.S. Cl.
CPC .... *A61M 15/0021* (2014.02); *A61M 15/0065* (2013.01); *A61M 15/0068* (2014.02); *A61B 5/0002* (2013.01); *A61B 5/4839* (2013.01); *A61M 2205/18* (2013.01); *A61M 2205/27* (2013.01); *A61M 2205/276* (2013.01); *A61M 2205/35* (2013.01); *A61M 2205/3546* (2013.01); *A61M 2205/3553* (2013.01); *A61M 2205/3569* (2013.01); *A61M 2205/3576* (2013.01); *A61M 2205/3584* (2013.01); *A61M 2205/3592* (2013.01); *A61M 2205/50* (2013.01); *A61M 2205/52* (2013.01); *A61M 2205/60* (2013.01); *A61M 2205/6009* (2013.01); *A61M 2205/609* (2013.01); *G16H 10/60* (2018.01)

(58) Field of Classification Search
CPC ............ A61M 15/0071; A61M 15/008; A61M 15/0081; A61M 15/0083; A61M 15/009; A61M 15/08; A61M 2202/0241; A61M 2205/18; A61M 2205/27; A61M 2205/276; A61M 2205/3379; A61M 2205/35; A61M 2205/3546; A61M 2205/3553; A61M 2205/3569; A61M 2205/3576; A61M 2205/3584; A61M 2205/3592; A61M 2205/52; A61M 2205/50; A61M 2205/60; A61M 2205/6009; A61M 2205/6063; A61M 2205/6072; A61M 2205/609
See application file for complete search history.

(56) References Cited

U.S. PATENT DOCUMENTS

| | | | |
|---|---|---|---|
| 6,202,642 B1 | 3/2001 | McKinnon et al. | |
| 6,958,691 B1 | 10/2005 | Anderson et al. | |
| 7,331,340 B2 | 2/2008 | Barney | |
| 7,454,267 B2 | 11/2008 | Bonny et al. | |
| 8,807,131 B1 | 8/2014 | Tunnell et al. | |
| 8,910,630 B2 | 12/2014 | Todd | |
| 9,775,379 B2 | 10/2017 | Davidson et al. | |
| 9,802,011 B2 | 10/2017 | Davidson et al. | |
| 9,888,725 B2 | 2/2018 | Cameron et al. | |
| 2002/0000225 A1 | 1/2002 | Schuler et al. | |
| 2003/0011476 A1 | 1/2003 | Godfrey | |
| 2003/0183226 A1* | 10/2003 | Brand | A61M 15/0065 128/200.23 |
| 2004/0139966 A1* | 7/2004 | Hodson | A61M 15/009 128/200.23 |
| 2005/0066961 A1 | 3/2005 | Rand | |
| 2006/0099149 A1* | 5/2006 | Patel | A61K 9/008 424/45 |
| 2006/0213506 A1* | 9/2006 | Hodson | A61M 15/009 128/200.14 |
| 2007/0163583 A1 | 7/2007 | Brand et al. | |
| 2007/0251950 A1 | 11/2007 | Bacon et al. | |
| 2009/0194104 A1 | 8/2009 | Van Sickle | |
| 2013/0087142 A1* | 4/2013 | Kane | A61M 15/009 128/200.23 |
| 2014/0190496 A1 | 7/2014 | Wensley et al. | |
| 2014/0322682 A1 | 10/2014 | Baym et al. | |
| 2014/0216444 A1 | 11/2014 | Shtram et al. | |
| 2015/0216237 A1 | 8/2015 | Wensley et al. | |
| 2016/0082208 A1* | 3/2016 | Ballam | A61M 16/0003 128/200.14 |
| 2016/0157524 A1 | 6/2016 | Bowen et al. | |
| 2016/0325058 A1 | 11/2016 | Samson et al. | |
| 2016/0363572 A1 | 12/2016 | Blackley | |
| 2016/0370337 A1 | 12/2016 | Blackley | |
| 2016/0370340 A1 | 12/2016 | Blackley | |
| 2017/0020195 A1 | 1/2017 | Cameron | |
| 2017/0027229 A1 | 2/2017 | Cameron | |
| 2017/0042215 A1 | 2/2017 | Murison | |
| 2017/0135410 A1 | 5/2017 | Cameron | |
| 2017/0136193 A1 | 5/2017 | Cameron | |
| 2017/0147787 A1* | 5/2017 | Albrecht | G06F 19/3468 |
| 2017/0181474 A1 | 6/2017 | Cameron | |
| 2017/0235918 A1 | 8/2017 | Hagen et al. | |
| 2017/0304563 A1 | 10/2017 | Adelson | |
| 2017/0304567 A1 | 10/2017 | Adelson | |
| 2017/0319797 A1 | 11/2017 | Germinario et al. | |
| 2018/0043114 A1 | 2/2018 | Bowen et al. | |
| 2018/0052964 A1 | 2/2018 | Adelson | |
| 2018/0221600 A1* | 8/2018 | Shears | A61M 11/00 |
| 2019/0111220 A1* | 4/2019 | Richardson | A61M 15/009 |

FOREIGN PATENT DOCUMENTS

| | | |
|---|---|---|
| EP | 2654864 A2 | 10/2013 |
| WO | 2002078595 A2 | 10/2002 |
| WO | WO2017015303 A2 | 1/2007 |
| WO | 2016064908 A1 | 4/2016 |
| WO | 2016187110 A1 | 11/2016 |
| WO | 2016187156 A1 | 11/2016 |
| WO | 2017137424 A1 | 8/2017 |
| WO | 2017192782 A1 | 9/2017 |
| WO | 2017182975 A1 | 10/2017 |
| WO | 2017182976 A1 | 10/2017 |
| WO | 2017205692 A1 | 11/2017 |
| WO | 2018033819 A1 | 2/2018 |

OTHER PUBLICATIONS

Ephrat Livni, A new 3D-printed cannabis inhaler lets doctors administer medical marijuana remotely, Jan. 1, 2017.
Syqe Medical, The World's First Selective-Dose Pharmaceutical Grade Medicinal Plants Inhaler.
Heather Mack, Thirty-six connected health apps and devices the FDA cleared in 2016, Dec. 30, 2016.
Vaporsmooth, Breeze Smart Inhaler—New Breeze Vaporizer by Resolve Digital Health.
Andrew Wagner, Asthma patients breathe easier with new bluetooth inhalers, PBS News Hour, www.pbs.org, May 10, 2017.
PCT/US2019/017093, PCT International Search Report, dated May 31, 2019.

* cited by examiner

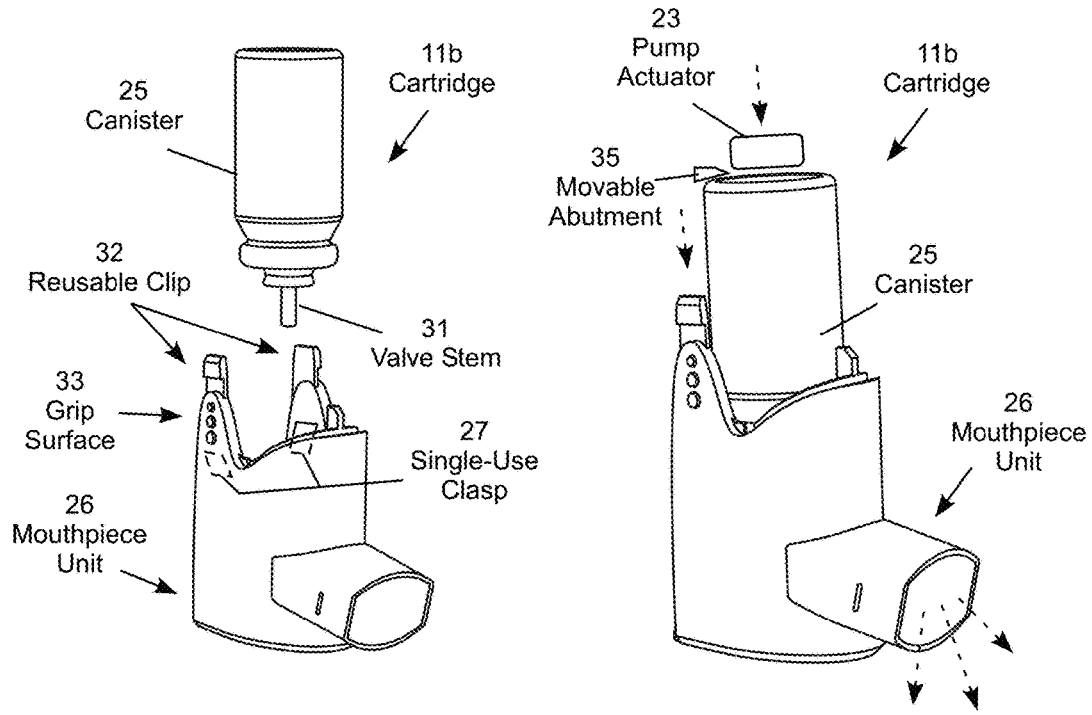
FIG. 3A
FIG. 3B
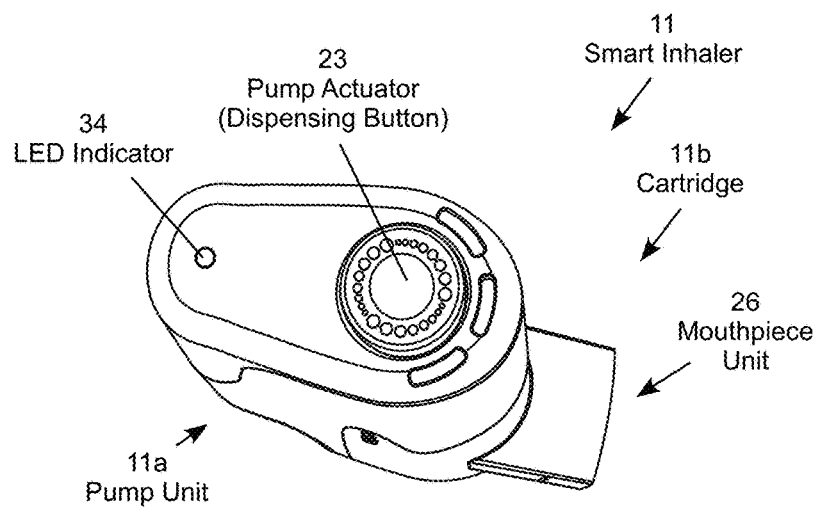
FIG. 3C

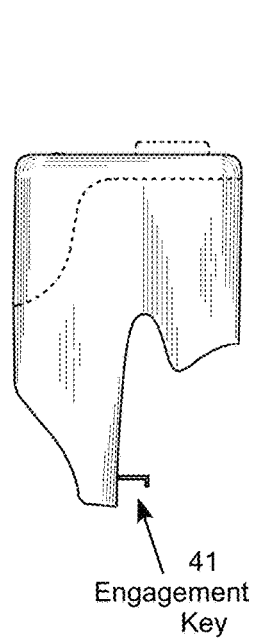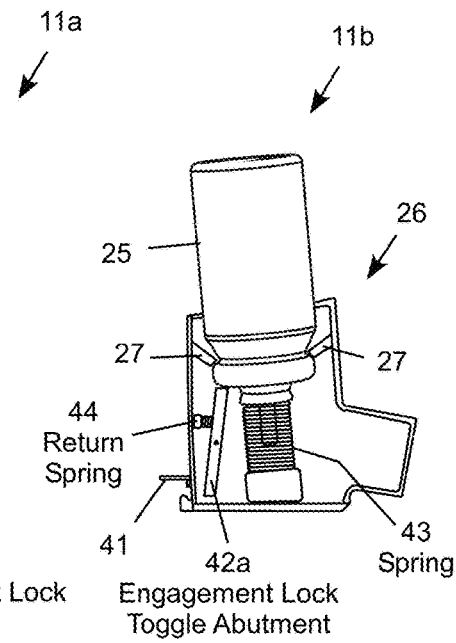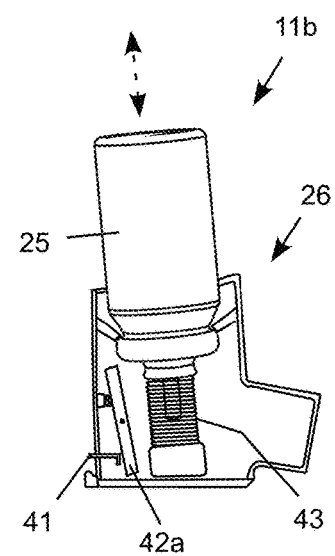
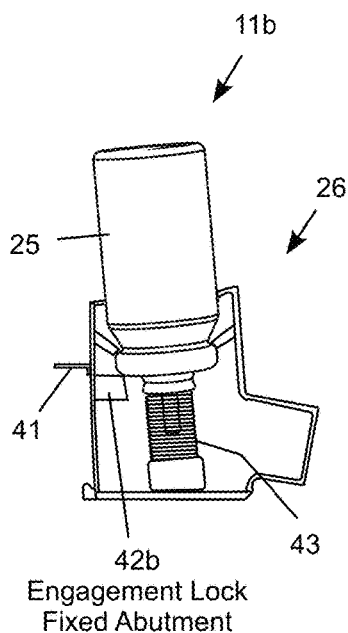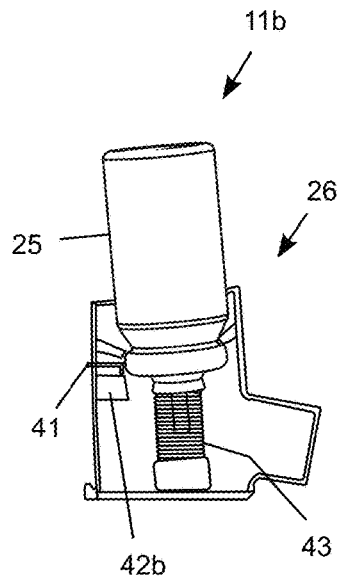
FIG. 4A  FIG. 4B  FIG. 4C
FIG. 4D  FIG. 4E

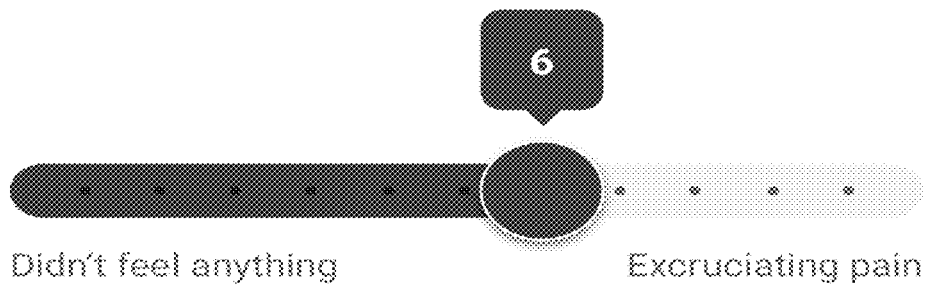
Describe in your own words how you are feeling, any recent changes, and how well you believe the treatment is working
[user input]  1701
1702a  1702b  1702c  1702n
FIG. 17

SECURITY FEATURES FOR AN ELECTRONIC METERED-DOSE INHALER SYSTEM

REFERENCE TO RELATED APPLICATION

This application claims priority to commonly owned U.S. Provisional Application Ser. No. 62/628,102 filed on Feb. 8, 2018 and 62/644,837 filed on Mar. 19, 2018, which are incorporated by reference.

TECHNICAL FIELD

The present invention is directed to security features for an electronic metered-dose inhaler and related systems suitable for monitored and controlled human inhalation of aerosol products without burning or vaporizing the products.

BACKGROUND

Physicians, clinical trial administrators, and product formulators lack effective security mechanisms for ensuring that patients and clinical trial participants taking self-administered medications and other products adhere to medical prescriptions and clinical trial protocols. They also have very limited product delivery choices for ensuring the delivery of precise amounts of medicine and other products that are self-administered by patients and clinical trial participants. Conventional delivery systems for products under prescription and clinical study, such as medication, nicotine, herbal products, pain killers, sleep aids, dietary stimulants, dietary suppressants, etc., also lack effective security mechanisms to prevent unauthorized product use and confirm that only the authorized user has taken an authorized product in accordance with an authorized protocol. This hampers the ability of physicians, clinical trial administrators, and product formulators to assess patient absorption rates, product efficacy, side effects, and optimize product formulations and dispensing techniques. They also lack effective, secure and authenticated electronic techniques for gathering per-dose data and user feedback related to the benefits and side effects from in-home, self-administrated products. This need applies generally to many types of products under prescription, clinical trial, or experimental testing.

As medical marijuana ("MMJ") continues to become legalized across the United States and worldwide, physicians prescribing MMJ treatment options for select patients will benefit from understanding the MMJ product options and medicines available by licensed MMJ cultivators and formulators. Conventional technology does not provide an automatically updated database of available MMJ medicines and patient efficacy information that physicians can reference to assist in making informed decisions when selecting MMJ formulations and treatment regimes. Traditionally, doctors refer to the Physician's Desk Reference ("PDR") for guidance on selecting and prescribing medications. But the current PDR does not even contain a category for MMJ. A need therefore exists for new techniques to provide physician guidance to assist in identifying patient conditions suitable for MMJ treatment and prescribing MMJ products well suited to the specific needs of patients with various conditions.

At the same time, a wide range of MMJ products are continually being developed containing precise strains of cannabis and carefully crafted combinations of cannabinoid extracts formulated and tested to be effective for specific ailments. For example, specific MMJ formulations are in various stages of development, clinical testing, approval and deployment for epilepsy, insomnia, intractable pain, migraine headaches, PTSD, Parkinson's, essential tremor, and other ailments. Typically, each ailment is most responsive to a specific MMJ formulation, and the search for specific MMJ formulations to treat a range of ailments is an ongoing industry focus. While many of these conditions are very serious and in desperate need of effective treatments, the MMJ products under consideration are generally considered relatively benign as compared to many other types of medications under development, such as chemotherapies. Less stringent clinical trial and experimental product testing procedures, such as in-home, patient-administered options, may therefore be considered appropriate for MMJ formulations. But cannabis is a well-known recreational drug and there are no in-home, patient-administered MMJ administration systems currently available that provide adequate safeguards to ensure that only authorized patients take the cannabis medications according to authorized protocols.

Another major challenge within the MMJ industry is that there are no consistent and very precise dispensing and delivery methods for MMJ products that can be recommended with confidence by physicians to their patients. Simply instructing patients to smoke a quantity of cannabis flower produces widely varying results among patients. Smoking cannabis is the most unsafe method for consuming the drug due to the carbonization of plant material during the combustion phase. The majority of states that allow MMJ use therefore do not permit the sale or medicinal use of plant material (leaves/flowers/buds) for smoking. Most states instead require the MMJ processors to use extraction processes that remove the beneficial oils from the plant material to form a liquid concentrate of cannabinoids and terpenes. This oil can then be used to produce alternate forms of MMJ consumption. One common method of prescribing the oil is in the form of a vape pen, similar to an electronic cigarette. The oil is combined with a carrier agent and then package in a cylindrical cartridge that contains an internal heating coil. The cartridge is then attached to a battery powered device which heats the coil to a high temperature to vaporize the mixture, allowing the patient to inhale the oil. Again, the heat required to vaporize the oil destroys many of the beneficial cannabinoids in the oil. Other factors that negatively affect the ability to control dispensing through inhalation include inconsistent inhalation depth and duration by the patient (long or short inhale), how long the inhaled product is held in the lungs by the patient (2 seconds or 20 seconds). The primary advantage to smoking or vaping MMJ is that "time to onset" is relatively quick and the effects of the MMJ is generally felt by the patient in only a few minutes. Ingesting edible MMJ products typically has a much longer time to onset, up to an hour, as well as a longer duration of the effect.

Other types of MMJ products include packaging the extracted oils in gel tablets, tinctures in glass bottles with eye droppers or in the form of edible products. The quantity of MMJ product ingested by the patient is virtually impossible to verify, as is the amount of the prescribed product that makes it through the patient's digestive system and into the bloodstream. Stomach acids destroy and the liver filters out many of the beneficial cannabinoids in the medicine. For example, when a patient ingests a 10 mg gel tab, after traveling through the digestive tract, only 15% to 30% of the medicine is typically absorbed into the bloodstream. MMJ ingestion again poses challenges for physicians in controlling accuracy and consistency in the delivery of the medicine. Bioavailability is also heavily impacted when smoking or vaping MMJ because the amount of cannabinoids that are destroyed or damaged by combustion or extreme heating is significant. A need therefore exists for new MMJ product delivery techniques that do not rely on burning or vaporizing the MMJ product at the time of consumption.

SUMMARY

The present invention meets the needs described above through security features for an electronically controlled metered-dose inhaler ("smart inhaler") and related systems and methods for delivering, controlling and monitoring aerosol products, such as MMJ medications. While the smart inhaler system is well suited for delivering MMJ products, it may be used to deliver any type of product suitable for aerosol administration including other types of medication and non-medical products, such as nicotine, herbal products, pain killers, sleep aids, dietary stimulants, dietary suppressants, and so forth. The smart inhaler system provides a robust, network-based system for in-home, patient-administered medications and other products for monitoring disease (or other condition) progression, conducting clinical trials, developing new drugs, evaluating experimental drugs, and so forth. Many of system innovations described in this disclosure are not limited to aerosol inhalers and may be applicable to other types of electronically-controlled, network-connected "smart delivery" devices, such smart nebulizers (e.g., vape pens), potable liquid dispensers, intravenous units, and other in-home, patient-administered delivery devices.

It will be understood that specific embodiments may include a variety of features in different combinations, as desired by different users. The specific techniques and structures for implementing particular embodiments of the invention and accomplishing the associated advantages will become apparent from the following detailed description of the embodiments and the appended drawings and claims.

BRIEF DESCRIPTION OF THE FIGURES

The numerous advantages of the smart inhaler may be better understood with reference to the accompanying figures in which:

FIG. 3A is a perspective view of the cartridge illustrating the aerosol canister separated from the mouthpiece unit.

FIG. 3B is a perspective view of the cartridge illustrating the aerosol canister installed in the mouthpiece unit.

FIG. 3C is a perspective view of the smart inhaler illustrating the cartridge installed into the pump unit.

FIG. 4A is a side view of the pump unit illustrating a key for an engagement lock.

FIG. 4B is side sectional view of the cartridge illustrating a toggle abutment engagement lock abutment in a locked position.

FIG. 4C is side sectional view of the cartridge illustrating the toggle abutment engagement lock in an unlocked position.

FIG. 4D is side sectional view of the cartridge illustrating a fixed abutment engagement lock in a locked position.

FIG. 4E is side sectional view of the cartridge illustrating the fixed abutment engagement lock in an unlocked position.

FIG. 17 is a conceptual illustration of a user interface displayed by the mobile app for receiving multi-media and interactive user feedback.

DETAILED DESCRIPTION

Figure 1:
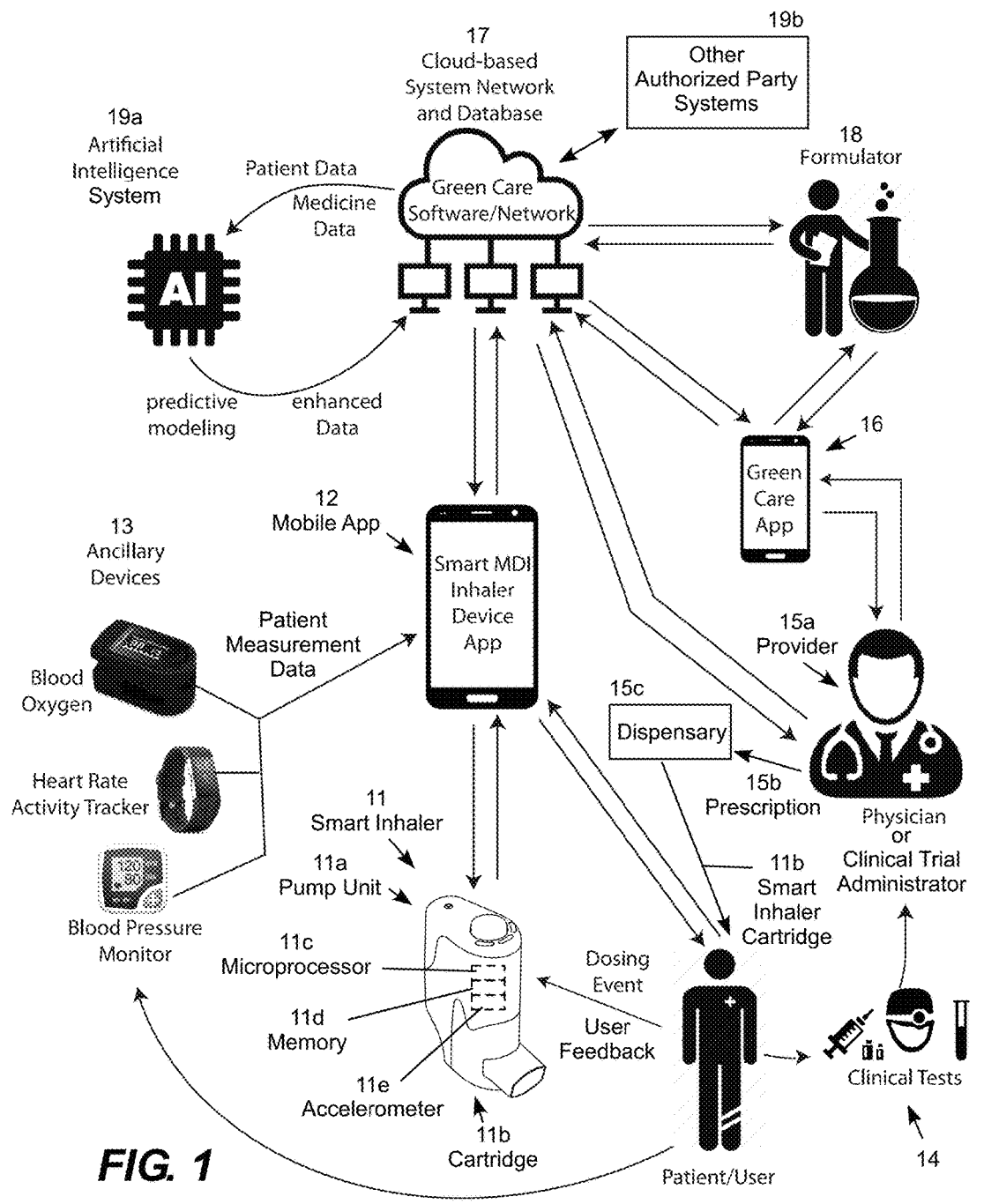
FIG. 1 is block diagram of a smart metered-dose inhaler system.

Embodiments of the smart inhaler system include an electronically controlled metered-dose inhaler device (referred to as the "inhaler," "smart inhaler," "MDI" or "SMDI") and related systems and methods that securely controls, monitors, and gathers user feedback and auxiliary device data, such as blood pressure, heart rate, and blood glucose data, related to inhaler usage. The system provides the gathered data for review and analysis by monitors, such as formulators of medications (and other inhalant products), prescribing physicians, clinical trial administrators, artificial intelligence, researchers, developers, facility operators, parents, guardians, authorities, and other authorized parties. The smart inhaler is specifically designed to administer aerosol products without the need to burn, vaporize, combine or otherwise prepare the products, other than by shaking the inhaler, at the time of inhaler use. The smart inhaler also ensures proper shaking prior to unlocking the inhaler for a dosing event.

The smart inhaler is suitable for administering MMJ protocols but is not limited to MMJ or other prescribed medications. The smart inhaler can be used to administer any type of inhaler protocol, such as medical prescriptions, clinical trials, and other protocols related to rehabilitation, addiction withdrawal, exercise, diet, safety testing, efficacy testing, judicial supervision, and so forth. The specific examples described in this disclosure are well suited to administering a wide variety of aerosol products in a range of protocols specifying dosing event quantities and time schedules. For example, the smart inhaler system could be used to administer nicotine, herbal products, anesthesia, and other non-medication type products. The smart inhaler system also allows medical prescriptions and other protocols to be changed remotely, typically in response to user feedback received in the course for the protocols. While the innovations have wider applicability, the illustrative embodiments are specifically designed for administering aerosol cannabis medications without the need to heat or vaporize the medication as part of inhalant administration.

The smart inhaler system presents tremendous opportunities for secure, per-dose monitoring of in-home, patient-administered medications and other products for monitoring disease (or other condition) progression, conducting clinical trials, developing new drugs, evaluating experimental drugs, and so forth. Many of the system-based and cloud-based innovations described in this disclosure are not limited to an inhaler and the product administering device and, as such, may be applicable to electronically controlled nebulizers (vape devices), potable liquid dispensers, intravenous units, and other types of product delivery devices.

The representative embodiment includes multiple security features, including features implemented by an electronically-controlled smart inhaler that reads electronically-readable canister information carried on the cartridge (i.e., on the canister or on the mouthpiece carrying the canister), features implemented by an a mobile app running on a user's mobile communication device (e.g., smartphone), and features implemented by a number of network resources referred to collectively as the "cloud." The cloud may include a wide range of databases and systems. The examples illustrated by the specific embodiments include systems operated by the formulator (e.g., manufacturer of the canister contents), the provider (e.g., prescribing physician or clinical trial administrator), dispensaries (including mail order dispensaries) that issue pump units and cartridges to users, and artificial intelligence platforms that analyze smart inhaler and related data from multiple users to identify medically significant factors and trends for use in efficacy analysis and the development of new protocols and formulations.

The smart inhaler system also integrates a range of auxiliary monitoring devices used to collect diagnostic data from a user in the course of a protocol. Representative auxiliary devices include a blood oxygen monitor, heart rate activity monitor, respiration monitor, blood pressure monitor, body temperature thermometer, blood glucose monitor, and so forth. The mobile app gathers and correlates the smart inhaler data with the measurement data from the auxiliary devices, for example by synchronizing, scaling and organizing the data for combined display on a common chart or time scale. The smart inhaler data set may be augmented with other diagnostic data obtained separately, such as MRI, CAT, X-ray, EKG, EEG, genome sequencing, medical history, family medical history, etc. Additional analysis conducted by the mobile app or cloud systems help to reveal the effect of the products delivered through inhaler operation on the user, which is typically reflected by the measurement data obtained by the auxiliary monitoring devices.

The smart inhaler system includes a number of safeguards to ensure that the inhaler is only used by the authorized user in an authorized manner. This makes the smart inhaler system suitable for use in many applications where security is an important factor. For example, a smart inhaler may be used to ensure that a controlled substance or prescription medication is only administered to the proper patient in accordance with a proper prescription. This address the several problems with conventional medication delivery systems, such as another person surreptitiously taking the patient's medication, the patient selling or giving the medication to someone else, the patient not taking the medication in accordance with the prescription, use of expired prescriptions, effectively administering product recalls, and effectively administering clinical trials. The inhaler pump unit may be issued separately (e.g., when a prescription, clinical trial or other protocol is initiated), while the cartridges will typically be issued separately and more frequently (e.g., each time a protocol cartridge is refilled). The inhaler pump unit is therefore designed to be used for many canisters, while each mouthpiece units is designed to be used with a single canister as a one-time use disposable cartridge. If desired, the same inhaler can be configured, for example through the use of passwords, MMJ Registration Card numbers, and bio-identifiers together with reading of cartridge (canister) information and prescription verification, to handle multiple prescriptions for individual or multiple persons. Bluetooth® pairing, along with cartridge and prescription verification, allows the same inhaler pump unit to be configured to communicate with multiple apps running on different mobile devices registered to different users. For example, a single pump unit could be used to administer products to multiple patients or clinical trial subjects who travel to the same location for inhaler use.

The smart inhaler system includes several different types of safeguards. Particular embodiments may include one or more of these safeguard features, and each inhaler need not include all or any particular combination of these features. A specific smart inhaler is typically registered to work only with a specific mobile device, as controlled by a mobile app running on the mobile device. A user's smart inhaler pairs with the user's mobile communication device, typically through a Bluetooth link, to verify that the inhaler is registered to the user, and that the canister corresponds to a valid prescription written for the user. Although the user's smart inhaler may operate according to a verified prescription without connecting to the user's mobile device at the time of product administration, it must be connected at some point prior to initial product administration to confirm that the canister in the user's inhaler corresponds to the user's prescription. The mobile app keeps track of the number of doses taken and the number remaining in the canister. The inhaler and the mobile app provide a variety of notifications indicating that a dosing window is open, the canister is nearing empty, the canister is empty, and when the canister is placed into a locked-out state for a number of different reasons. For example, the inhaler may be locked-out for use with a particular cartridge because it is not loaded with a verified cartridge, the cartridge has been recalled or expired, there are no more doses remaining in the canister, or when unauthorized use has been detected or been attempted. In a particular embodiment intended for a child or elderly person's inhaler, voice notifications may be played in a voice familiar to the user. Notifications or alarms may also be sent by voice message, text message, email or other techniques to a communication device associated with an authorized third party, such as a parent, guardian, physician or care taker. In another embodiment intended for clinical testing, notifications or alarms may be automatically sent to the administrator of the clinical trial.

In addition, there three types of physical locks available, a single-use clasp in the mouthpiece, a dispensing button lock, and an engagement lock. The single-use clasp allows a canister to be inserted into the mouthpiece unit one time, and then breaks away to disable the mouthpiece if the canister is removed from the mouthpiece. This effectively configures the mouthpiece as a disposable unit restricted to working with a single canister. The dispensing button lock includes a movable abutment controlled by the microprocessor in the pump unit that only allows the dispensing button to be depressed to dispense product from the canister in accordance with a valid and verified protocol. The engagement lock includes an abutment in the mouthpiece that prevents product from being dispensed from the canister when the mouthpiece is not installed in the pump unit. This prevents unauthorized persons from circumventing the dispensing button lock by manually depressing the canister into the mouthpiece when the mouthpiece is not installed in the pump unit.

The cartridge, consisting of a canister installed in a mouthpiece unit, carries an electronically readable label or chip with information about the product in the canister, such as a medication description. The pump unit will not work with a cartridge until the cartridge has been validated with a prescription (or other protocol) for use by the user. Cartridge verification requires the pump unit to read canister information stored by a cartridge memory carried by the cartridge. The pump unit must also become paired with and interact with the mobile app running on a mobile device that is registered for use with that specific pump unit (or canister in a multi-user embodiment). This requires matching the cartridge with a valid prescription (or other protocol) written for the authorized user of the inhaler. While the pump unit reads the cartridge information from the cartridge memory, the user's prescription (or other protocol) is typically obtained from another location, such as the cloud via the mobile app running on the user's mobile device.

An authorized user may also be required to enter pre-dose identification information, such as a password, MMJ Registration Card number, or bio-identifier (e.g., fingerprint, retina scan, etc.), to activate the inhaler. The user may also be required to enter post-dose feedback through the mobile app, which may include providing a written account, picture, photo, chat or other multi-media or interactive feedback. The post-dose feedback may be required immediately after taking a dose and at one or more other times following a dose. The post-dose feedback may be used to detect suspected fraudulent or improper use of the inhaler, which causes the inhaler to enter a locked-out state until the suspected fraud or improper use has been resolved. Feedback received from the mobile app can be used for a number of other purposes including dose confirmation, prescription modification, and analyses of medication efficacy, side effects, time to onset, and so forth. Feedback from multiple users may be used to create a multi-user, multi-product database for further analysis including analysis by artificial intelligence and other researchers.

Illustrative embodiments of the smart inhaler and related systems and methods are described below with reference to the appended figures. FIG. 1 is conceptual block diagram of a smart metered-dose inhaler system 10. In the illustrative embodiments, the user's mobile app 12 (denoted as the "Smart MDI Inhaler Device App"), the mobile app 16 (denoted as the "Green Care App") used by the physician or clinical trial administrator 15a, a similar app used by the formulator 18, an artificial intelligence platform 19a, and platforms associated with other authorized parties 19b (e.g., researchers, developers, parents, guardians, care takers, judicial supervisors, parole officers, addiction recovery monitors, etc.). These online systems communicate with each other through a cloud-based network and database 17 (also referred to as the "cloud" for shorthand, denoted as the "Green Care Software/Network") to exchange information related to use of the smart inhaler 11. It will be understood that the actions performed by the patient are generally performed through user interaction with the mobile app 12 or in some cases the smart inhaler 11 (unless otherwise noted or connoted by the context), and that actions performed by the provider are generally performed through interaction with the online provider system 15a via the mobile app 16 (unless otherwise noted or connoted by the context). Similarly, actions performed by the patient on the provider system 15a are performed through network communications between the mobile app 12 and the mobile app 16 over the cloud 17. In the same vein, actions performed by the formulator are generally performed through an online formulator platform 18 over the cloud 17 (unless otherwise noted or connoted by the context), and so forth.

A central feature of the system 10 is an electronically-controlled, hand-held, smart metered-dose inhaler 11, which includes a pump unit 11a and a removable cartridge 11b that includes a mouthpiece unit carrying a canister (see FIGS. 2A-2B) filled with an aerosol product of interest (e.g., MMJ formulation) that is properly pressurized (e.g., to about 80 psi) with a medically safe inhalant (e.g., HFA-134a). The pump unit 11a includes an onboard microprocessor 11c, memory 11d, and accelerometer 11e. The accelerometer is used to detect that the smart inhaler has been adequately shaken as a condition for unlocking the inhaler to administer a dose. The smart inhaler 11 (or the cartridge in a multi-cartridge or multi-user embodiment) is registered for use with the mobile app 12 running on a mobile device associated with an authorized user. The mobile app 12 controls the smart inhaler 11 and also integrates information associated with operation of the inhaler with other information, such as medically relevant measurements obtained from ancillary devices 13. In this particular embodiment, the example ancillary devices 13 are represented by a blood oxygen monitor, a heart rate activity tracker, and a blood pressure monitor.

The mobile app 12 communicates over a suitable network (e.g., mobile telephone, private data network, Internet, intranet, ethernet, etc.) with the provider system 15a, which issues a prescription 15b for the user, which the user typically picks up or receives in the mail from a dispensary 15c. For example, the prescription 15b may be issued in the form a cartridge 11b including an aerosol medication canister held within a mouthpiece unit that is inserted into the pump unit 11a of the smart inhaler 11. This allows the same pump unit 11b to be used with many different cartridges including refill cartridges. The provider system 15a may obtain additional clinical tests 14 related to the user, such as blood tests, lab tests, and so forth. The provider system 15a also interacts with other elements of the system 10. For example, the provider system 15a typically orders medication cartridges with specific formulations from the formulator 18, which delivers prescribed cartridges to the dispensary 15c for delivery to the patient.

Ultimately, many smart inhalers, physicians, clinical trial administrators, formulators, AI platforms, researchers, and developers will be interconnected by the cloud 17 allowing a large body of clinical data to the gathered regarding inhaler use, user feedback, auxiliary device data, clinical tests, and other relevant data for use in prescribing medications and conducting research and development. This will include analyses conducted by artificial intelligence as wells as human R&D teams at universities, foundations, corporations, and so forth. The system 10 thus represents an important advancement in the field of MMJ because this type of data is currently lacking, while a wide range of MMJ products are currently being developed to treat a wide range of conditions. The system 10 also represents an important and more general advancement in security, monitoring and administration of prescriptions, disease (and other condition) progression, clinical trials, and experimental drug testing through distributed used of in-home, patient-administrated delivery devices.

To further advance the research and development process, the cloud 17 connects the elements of the system 10 with an artificial intelligence ("AI") system 19, which includes one or more platform and related software, which may include multiple AI platforms at various research universities, foundations and companies. Generally described, the AI system 19 receives patient medical data from the various systems interconnected by the cloud 17, applies predictive modeling, and provides enhanced data and predictive modeling results back to other cloud elements. This information can then be used to develop new MMJ formulations and protocols. The patient medical data supplied to the AI system 19 typically includes, but is not be limited to, device status, medication usage, dispensing habits, formulation efficacy, and patient feedback gathered on various devices and network servers. The AI system software automatically sorts, parses and analyzes all data and places it into unique categories. These categories may be created based on a variety of inputs, such as but not limited to, current medical diagnosis, physiological characteristics (age, weight, sex, race, health status, etc.), family medical history (mother, father, grandparents, etc.), DNA analysis (ancestry, genealogy, genetic predisposition to diseases/medical conditions), etc. The AI software analyzes all of these factors along with any other available data that could possibly impact the outcomes of treatment for each individual and then incorporate predictive modeling for improving efficacy of medications and treatment plans based on combinations of the patient inputs.

For example, when the AI software has processed and analyzed the available characteristics data from 200 individual patients suffering from multiple sclerosis (MS) in combination with their prescribed treatment plans, treatment adherence, prescribed medicine formulation(s), efficacy results and personal feedback and other input, the AI can then begin to model this data to predict how individuals will likely react to specific treatment plans for MS. Expanding on this example, when the AI has identified a treatment plan (e.g., specific formulation(s), dosing amounts, dosing frequency, duration of treatment, etc.) with a target success rate (e.g., 72%) for a specific group of patients suffering with MS and with very similar characteristics, the AI can generate an optimized medical cannabis treatment plan for physicians to administer and prescribe to new MS patients. This guidance in prescribing a treatment plan, with a high success rate, will eliminate relying on physicians to effectively guess at what may or may not be effective for an MS patient. With regards to the portion of MS patients that did not benefit from treatment plan under evaluation (i.e., the other the 28% in the example with a 72% success rate), the AI can make predictions and suggest to the formulator how a specific formulation can be adjusted and optimized for higher efficacy for these remaining patients. The AI may also provide suggestions to a physician on what aspects of a potential treatment plan may provide more benefits to these patients. As more efficacy data for MS patients is collected and analyzed, the AI predictive modeling for effective formulations and successful treatments plans for individual patients will become more accurate.

Figure 2A:
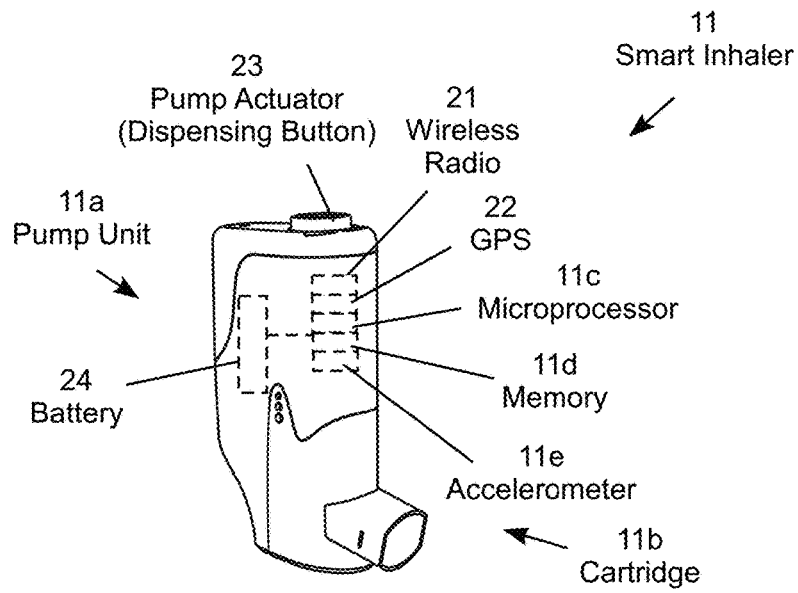
FIG. 2A is a perspective view of a smart inhaler.
Figure 2B:
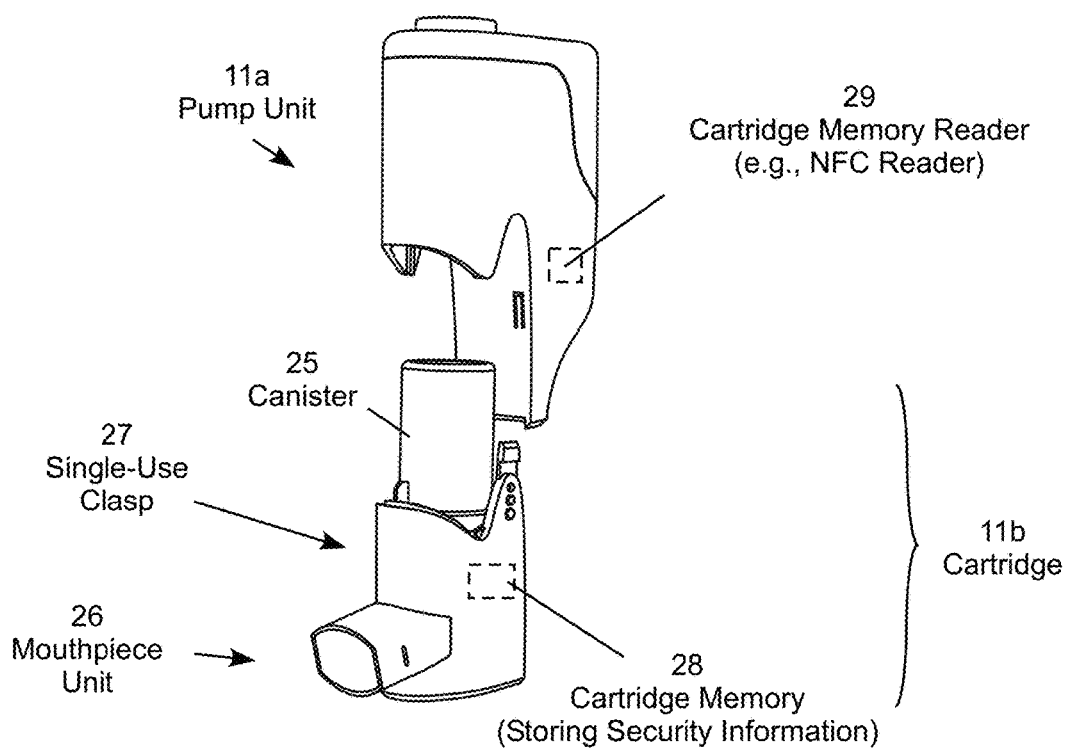
FIG. 2B is a perspective view of the smart inhaler illustrating a pump unit and a separate cartridge that includes a mouthpiece unit containing an aerosol canister.

FIG. 2A shows a representative embodiment of the smart inhaler 11, while FIG. 2B shows the smart inhaler with the pump unit 11a separated from the cartridge 11b. The pump unit 11a includes a pump actuator 23 (e.g., dispensing button), the microprocessor 11c, the memory 11d, and the accelerometer 11e described with reference to FIG. 1, which are powered by an onboard rechargeable battery 24. The battery 24 also powers an onboard wireless radio 21 and GPS unit 22. The wireless radio 21 is operative for pairing and communicating with the mobile app 12 running on the user's mobile device, and the GPS unit 22 allows the location of the inhaler 11 to be tracked by the mobile app 12. The wireless radio 21 and the GPS unit 22 also allow the location of the inhaler 11 to be tracked remotely by the provider system 15a (typically by the provider mobile app 16), the formulator system 18, the AI platform 19a and the other authorized party systems 19b as provided by an authorized protocol. This allows one or more of these systems to remotely monitor, enable and disable the smart inhaler 11, for example over the cloud 17 or another suitable network (e.g., mobile telephone, wireless data, 5G, Internet of things (IOT), etc.). The remote systems can also use the location of the smart inhaler 11, along with the locations of many other similarly equipped smart inhalers, as a demographic parameter for controlled substance monitoring, supervisory user monitoring, artificial intelligence, research, development, and other purposes in accordance with authorized protocols. The smart inhaler 11 may also carry other onboard devices powered by the battery 24 for user identification, security protocols, notifications, alarms and communications, such as a camera, speaker, microphone, vibrator, data encryption, personal health record storage, bio-identification (e.g., fingerprint reader, retina scanner, voice recognition, etc.) and other desired functionality.

The cartridge 11b includes a canister 25 that is permanently attached to a mouthpiece unit 26 by a single-use clasp 27. The single-use clasp 27 engages the canister 25 when the canister is initially installed into the mouthpiece unit 26 to prevent the canister from being removed from the mouthpiece unit without breaking the clasp, which disables the mouthpiece from operably receiving another canister. The single-use clasp 27 is a safety measure that effectively turns the mouth-piece into a disposable single-canister device. The cartridge 11b also includes a cartridge memory 28, such as a barcode, QR code, RFID tag, or NFC chip, that contains canister information including a description of the product contained in the canister 25. The single-use clasp 27 restricts the mouthpiece unit 26 to working with a single canister 25, which allows the cartridge memory 28 to be carried by the canister 25 or the mouthpiece unit 26, as desired. Thus, the cartridge memory 28 is typically encoded when the canister 25 is installed into the mouthpiece unit 26. The pump unit 11a includes a cartridge reader 29 powered by the onboard battery 24 that reads the cartridge memory 28 when the cartridge 11b is installed in the pump unit. The medication description may be directly stored by the cartridge memory 28, or the cartridge memory may store a code that the microprocessor 11c uses to look up (index) an associated medication description stored in the memory 11d (i.e., the memory may store an onboard medication index updated from the cloud 17 from time to time). Alternatively or additionally, the mobile app 12 may use the code to look up (index) an associated medication description stored in the cloud 17, for example in an online medication database associated with the formulator 18 or the provider 15a.

In particular embodiments, for example, the cartridge memory 28 may be a barcode, RFID tag, or NFC chip and the cartridge reader 29 may be an optical barcode reader, RFID reader, or NFC reader. In the barcode and RFID embodiments, the cartridge reader 29 is typically turned on momentary upon a cartridge being installed to allow the pump unit to read the cartridge memory 28. In an NFC embodiment, the NFC antenna in the cartridge is typically turned on momentary upon a cartridge being installed to allow the NFC reader in the pump unit to read the NFC tag. Upon successfully reading the tag data, the NFC antenna automatically turns off to conserve battery power until a new cartridge installation event.

The user pairs the microprocessor inside the pump unit 11*a* with the mobile device running the mobile app 12 (e.g., via Bluetooth link) to activate and control the smart inhaler 11. As a security measure, the mobile app 12 checks the registration information of the mobile device against the registration information of the smart inhaler 11 (or the specific canister 25 in a multi-user embodiment) to ensure that the inhaler is going to be used by an authorized user. The medication within the canister 25 is identified by the canister information stored by the cartridge memory 28. When the cartridge 11*b* is inserted into the pump unit 11*a*, the cartridge memory reader 29 in the pump unit reads the canister information from the cartridge memory 28, which is uploaded to the mobile app 12. The mobile app 12 also downloads the user's prescription from the provider system 15*a*. As another safeguard, the pump unit 11*a* keeps the pump actuator 23 locked (e.g., an abutment blocks the dispensing button) unless the mobile app 12 verifies that the product in the canister 25 corresponds to a valid prescription issued to the user verified through the provider system 15*a*. Upon verification of the user registered to the inhaler 11, a valid prescription issued to the same user, and determination that a dosing window is open in accordance with the prescription, the pump unit 11*a* unlocks the pump actuator 23 for a dosing event, for example by moving an abutment to unblock the pump actuator.

Figure 3D:
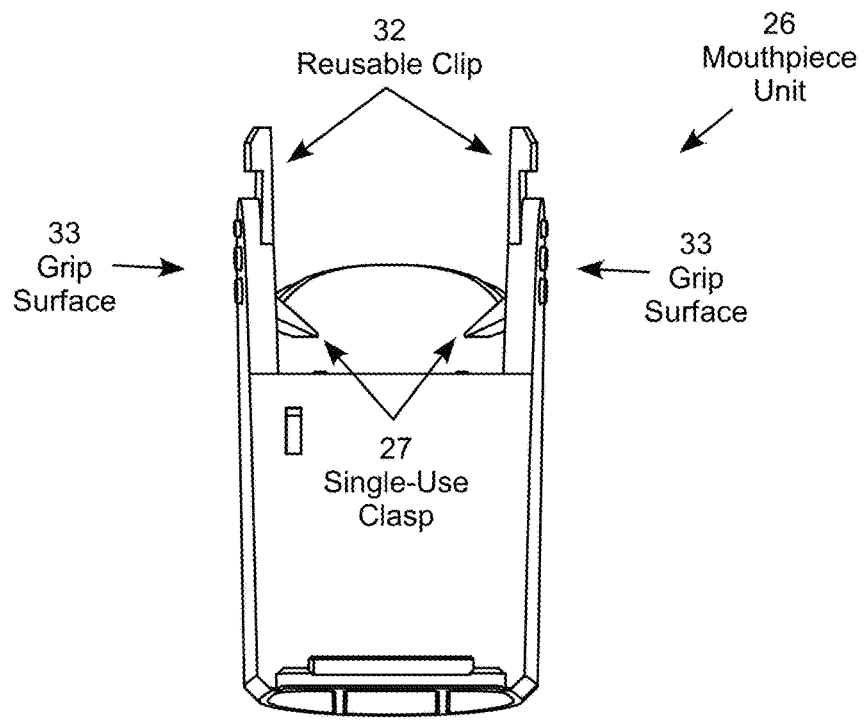
FIG. 3D a cut-away side view of the mouthpiece unit showing an illustrative embodiment of a single-use clasp.
Figure 3E:
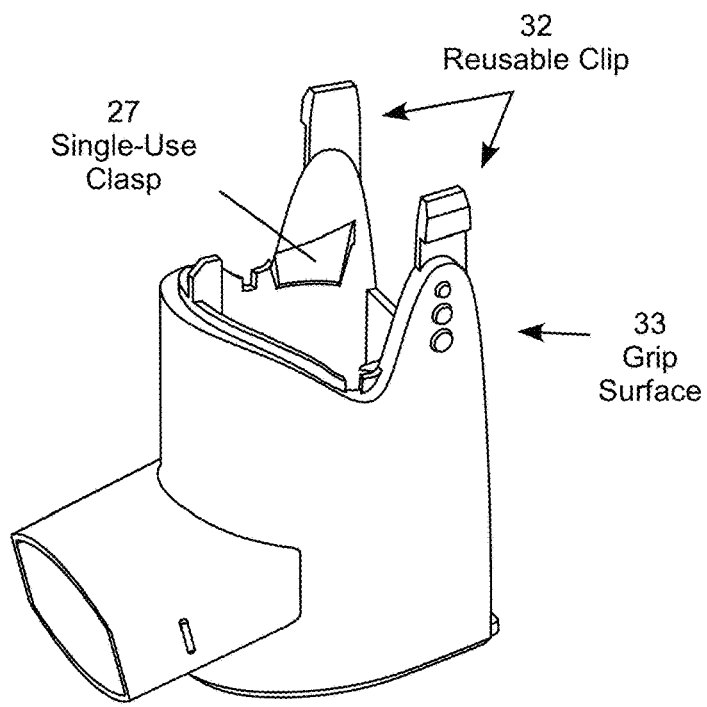
FIG. 3E is a perspective view of the mouthpiece unit showing the single-use clasp.

FIG. 3A shows the cartridge 11*b* with the aerosol canister 25 separated from the mouthpiece unit 26, while FIG. 3B shows the canister installed into the mouthpiece unit and FIG. 3C shows the smart inhaler 11 from above. FIG. 3D and FIG. 3E show the mouthpiece unit 26 including an illustrative embodiment of the single-use clasp 27. The canister 25 includes a valve stem 31 that dispenses a small quantity of the contents of the canister when the valve stem is pushed into the canister. When depressed, the pump actuator 23 pushes the canister 25 downward into the mouthpiece unit 26, which pushes the valve stem 31 into the canister 25 to release a small quantity of the contents of the canister through the mouthpiece unit. The microprocessor 11*c* controls the pump unit 11*a* to move an abutment 35 to block and unblock the pump actuator 23 to lock and unlock the inhaler 11. The pump action caused by depressing the pump actuator 23 may be controlled by an internal motor or by the user manually pressing down on the dispensing button. The mouthpiece unit 26 includes a reusable clip 32 for removably attaching the cartridge 11*b* to the pump unit 11*a* with the pump actuator 23 positioned to push the canister 25 into the mouthpiece unit 26 to dispense the contents of the canister through the mouthpiece. The user pinches a grip surface 33 adjacent to the clip 32 to remove the cartridge 11*b* from the pump unit 11*a*. The cartridge memory 28 carried by the cartridge 11*b* is positioned to be readable by the cartridge memory reader 29 carried by the pump unit 11*a* when the reusable clip 32 attaches the cartridge to the pump unit in an operable configuration in which the pump actuator 23 is positioned to reciprocate the canister 25 within the mouthpiece unit 26 to release the contents of the canister through the mouthpiece unit. The single-use clasp 27 includes a pair of flanges that are angled downward in the direction of insertion of the canister 25. The flanges bend slightly without breaking to allow the canister 25 to be inserted downward into the mouthpiece unit 26. The flanges break away, however, if the canister 25 is forced upward out of the mouthpiece unit 26.

The pump unit 11*a* also includes an LED indicator 34 powered by the onboard battery 24 that indicates the status of the pump unit. For example, the LED indicator 34 may be off when the smart inhaler 11 is locked between dosing events, may illuminate or flash green to indicate that the inhaler is unlocked and ready for a dosing event, and may illuminate or flash red when the smart inhaler is in a locked-out state. For example, the LED may illuminate or flash red to when the inhaler is locked-out due to a pairing failure caused by a mismatch between the inhaler (or canister) credentials and the user's credentials stored by the user's mobile unit. The inhaler may also lock-out due to a mismatch between the medication in the canister, as reflected by the canister memory, and the user's prescription or recall or expiration of the product in the canister. As additional examples, the inhaler may lock-out because the user has not entered required feedback for a prior dose, because fraudulent use or attempted misuse of the inhaler has been detected, due to a canister recall or expiration, or a change in prescription removing the user's authorization to take the medication in the canister. The LED may flash in different patterns to signify these different lock-out reasons. The LED indicator may also be augmented by audible alarms, a voice notification, or a vibration to indicate the inhaler status. The pump unit status may be accompanied by notifications displayed or played by the user's mobile device under the control of the mobile app 12. Voice notification by the pump unit or the mobile app may be particularly useful for children, elderly, and ill users who may be more likely to understand or comply with voice notifications in a familiar voice, such as notifications recorded in the voice of a parent, guardian, other family member, care taker, or physician.

FIG. 4A shows the pump unit 11*a* while FIGS. 4B-4E show cut-away views of the cartridge 11*b* illustrating an engagement lock that prevents the canister 25 from being manually depressed into the mouthpiece unit 26 to dispense the contents of the canister when the cartridge is not installed in the pump unit. As shown in FIG. 4A, the pump unit 11*a* includes an engagement lock key 41 that is inserted into the cartridge 11*b* when the cartridge is installed in the pump unit. As a first example, FIGS. 4B and 4C illustrate a toggle engagement lock. As shown in FIG. 4B, a toggle abutment 42*a* blocks the canister 25 from being pushed into the mouthpiece unit 26 when the key 41 is not inserted into the cartridge 11*b* because the cartridge is not properly installed into the pump unit. As shown in FIG. 4C, when the cartridge 11*b* is properly installed into the pump unit 11*a*, the key 41 releases the toggle abutment 42*a* to allow the canister 25 to be pushed into the mouthpiece unit 26. A spring 43 biases the cartridge 25 in a retraction direction so that the pump actuator can reciprocate the cartridge between the retraction direction (upward in figures) and an opposing insertion direction (downward in figures) to release a portion of the contents of the canister 25 each time the canister is reciprocated to dispense the contents of the cartridge through the mouthpiece unit 26. When the key 41 releases the toggle abutment 42*a*, a return spring 44 forces the toggle abutment to reengage the canister 25 to lock the cartridge.

As another example, FIGS. 4C and 4D illustrate a fixed abutment engagement lock. As shown in FIG. 4C, a fixed abutment 42b blocks the canister 25 from being pushed into the mouthpiece unit 26 when the key 41 is not properly inserted into the cartridge 11b. As shown in FIG. 4D, when the cartridge 11b is properly installed into the pump unit 11a, the key 41 pushes the canister 25 off the fixed abutment 42b to allow the canister to be pushed into the mouthpiece unit 26. The spring 43 biases the cartridge 25 upward so that the pump actuator can reciprocate the cartridge up and down to dispense the contents of the cartridge through the mouthpiece unit 26. When the key 41 is removed, the spring 43 forces the cartridge 25 to reengage the fixed abutment 42b to lock the canister. Other types of keys and abutments may be employed. For example, security may be enhanced through the use of more sophisticated keys, tumbler locks, magnetic locks, electronic locks, and so forth. As additional examples, the key could include an eccentric plate, multiple prongs, or movement in two or three dimensions making it more difficult for an unauthorized user to bypass or tamper with the engagement lock.

Figure 5:
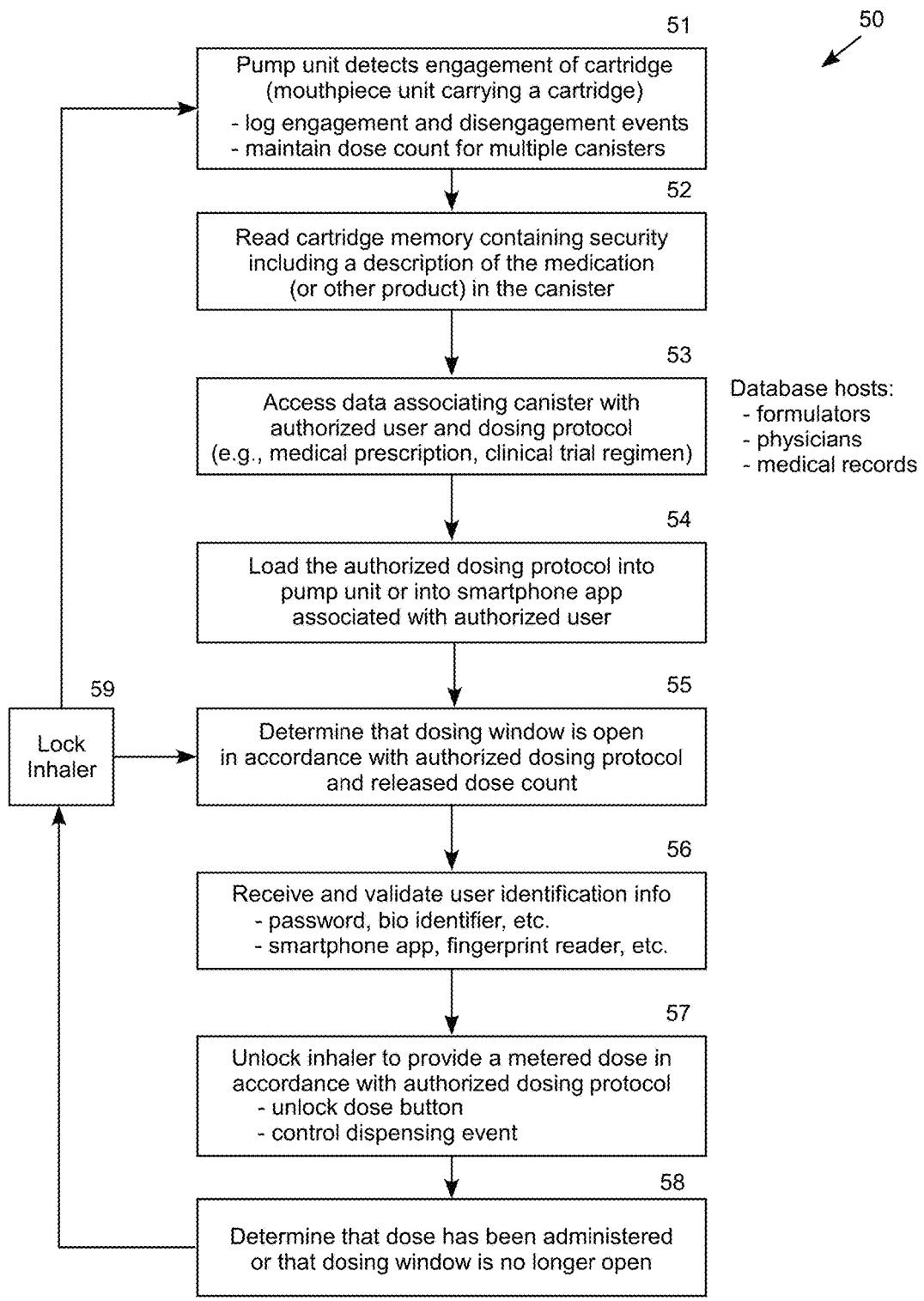
FIG. 5 is a logic flow diagram illustrating a security procedure for locking and unlocking the smart inhaler.

FIG. 5 is a logic flow diagram illustrating a security procedure 50 for locking and unlocking the smart inhaler. In step 51, the pump unit detects engagement of a cartridge, which includes a mouthpiece unit carrying a canister. The pump unit typically logs engagement and disengagement events and has the capability to maintain dose counts for multiple cartridges, which allows the same pump unit to be used to dispense multiple prescriptions for the same user. In addition, in a multi-user embodiment, the same pump unit may be use to dispense one or more prescriptions for multiple users. Step 51 is followed by step 52, in which the pump unit reads the cartridge memory containing security information including a description of the medication (or other product) in the canister. Alternatively, the cartridge memory may include a code that the pump unit or the user's smart inhaler or mobile app uses to look up the medication description. Step 52 is followed by step 53, in which the smart inhaler mobile app pairs with the pump unit and access data associating the product in the canister with an authorized user of the pump and a dosing protocol authorized for the user, such as a medical prescription or clinical trial regimen. If the product in the canister is validated for an authorized user, step 53 is followed by step 54, in which the pump unit loads the dosing protocol. The pump unit has sufficient onboard microprocessor, memory, and battery resources to store and administer the dosing protocol. The user's smart inhaler mobile app initially downloads the dosing protocol from a cloud-based system associated with the user's physician or clinical trial administrator. Once the smart inhaler mobile app verifies the dosing protocol, it is downloaded to the pump unit so that the pump unit can administer the protocol even when connectivity is not available between the pump and the user's smart inhaler mobile app.

Step 54 is followed by step 55, in which the pump unit determines that a dosing window is open in accordance with the verified dosing protocol. This typically includes unblocking the pump actuator for a designated number of puffs (e.g., pushes of the dispensing button) and activating notifications on the pump unit and the user's mobile device. The user's pump unit stores its own copy of the dosing protocol so that the pump unit can administer the protocol even when connectivity is not available between the pump and the mobile app. Step 55 is followed by step 56, in which the mobile app receives and validates user identification information, such as a password, MMJ Registration Card number, fingerprint, retina scan, photo, face scan, voice command, or other user identification. Step 56 is followed by step 57, in which the smart unit mobile app causes the pump unit to unlock for the dosing event, for example by removing an abutment that prevents the dispensing button from being depressed. Step 57 is followed by step 58, in which the pump unit determines that the dose has been administered or the dosing window has expired.

If connectivity exists between the pump unit and the smart inhaler mobile app, the pump unit uploads this information to the smart mobile unit in real-time time. Otherwise the pump unit uploads the information when connectivity is reestablished. Similarly, if connectivity exists between the smart inhaler mobile app and the cloud, the mobile app uploads this information in real-time to the cloud (e.g., with the online system operated by the user's physician or clinical trial administrator). Otherwise the mobile app uploads the information when connectivity is reestablished. Step 58 is followed by step 59, in which the pump unit locks the inhaler, for example by moving the abutment to prevent the dispensing button from being depressed. Following step 59, the routine 50 returns to step 55, in which the pump unit and mobile app wait for another dosing event. When another cartridge engagement is detected, routine 50 goes back to step 51 (cartridge engagement detected) and continues from there.

Figure 6:
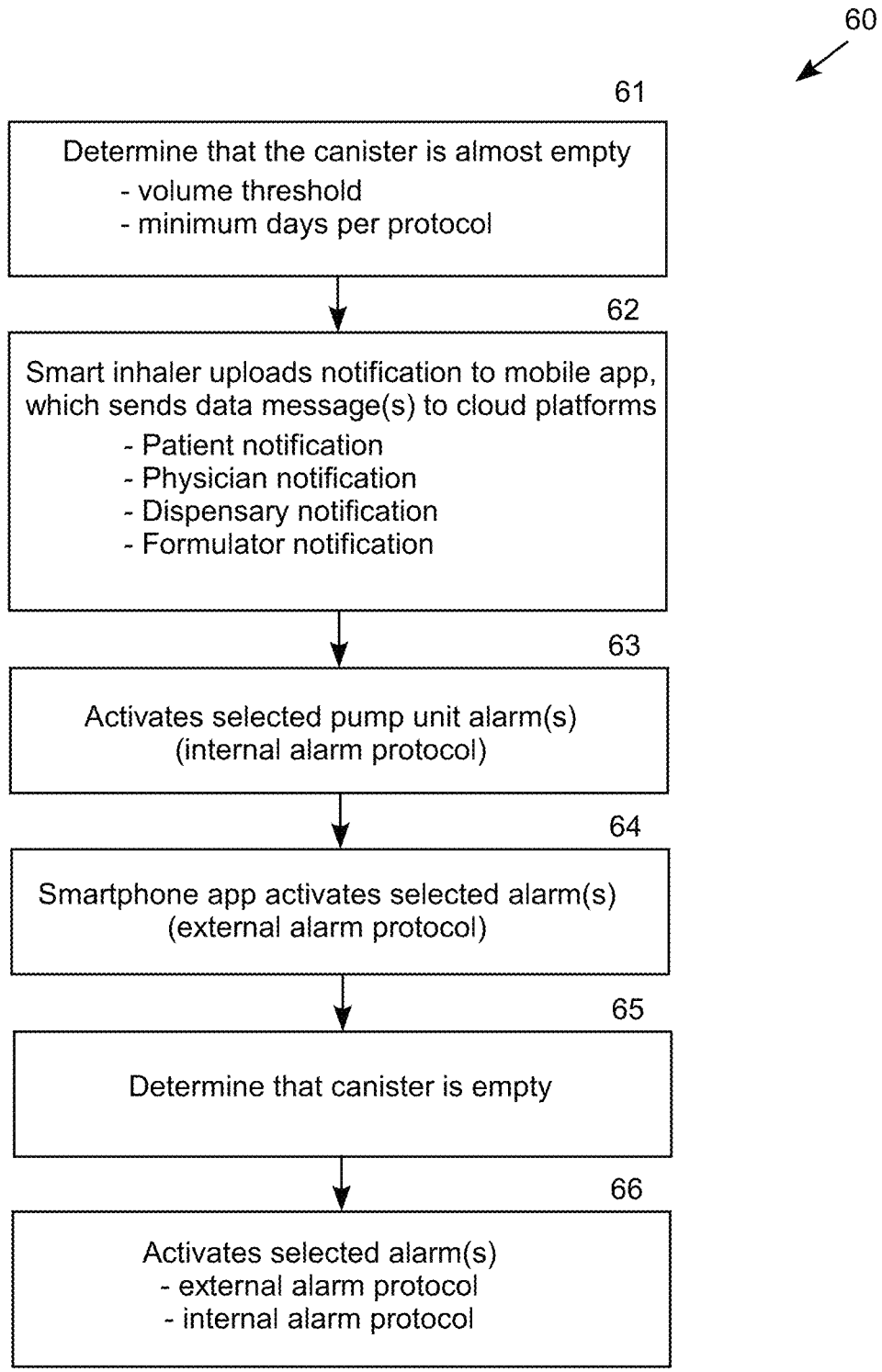
FIG. 6 is a logic flow diagram illustrating a procedure for notifying a user that the aerosol canister in the smart inhaler needs to be replaced.

FIG. 6 is a logic flow diagram illustrating a procedure 60 for notifying a user that the aerosol canister in the smart inhaler needs to be replaced. In step 61, the user's mobile app determines that the canister is almost empty. The mobile app may make this determination directly, or it may be made by the smart inhaler and uploaded to the user's mobile app. The determination may be based on a volume threshold (e.g., only 5 does left) or a minimum days remaining per the protocol (e.g., only 5 day left on protocol). Step 61 is followed by step 62, in which the user's mobile app sends a refill notification to one or more of the user's physician, clinical trial administrator, dispensary or formulator as appropriate to effect the refill. Step 62 is followed by step 63, in which the smart inhaler activates an internal alarm protocol, which includes one or more notifications on the pump unit, such as flashing LED, audible notification, vibration, etc. Step 63 is followed by step 64, in which the mobile app also activates an external alarm protocol including one or more notifications on the user's mobile phone (e.g., pop-up notification, status bar notification, calendar notification, etc.). Step 64 is followed by step 65, in which the smart inhaler or the mobile app determines that the canister is empty, typically by determining that no doses remain in the dosing protocol. Step 65 is followed by step 66, in which the smart inhaler activates an internal alarm protocol, and the mobile app activates an external alarm protocol, to notify the user that the canister is empty.

Figure 7:
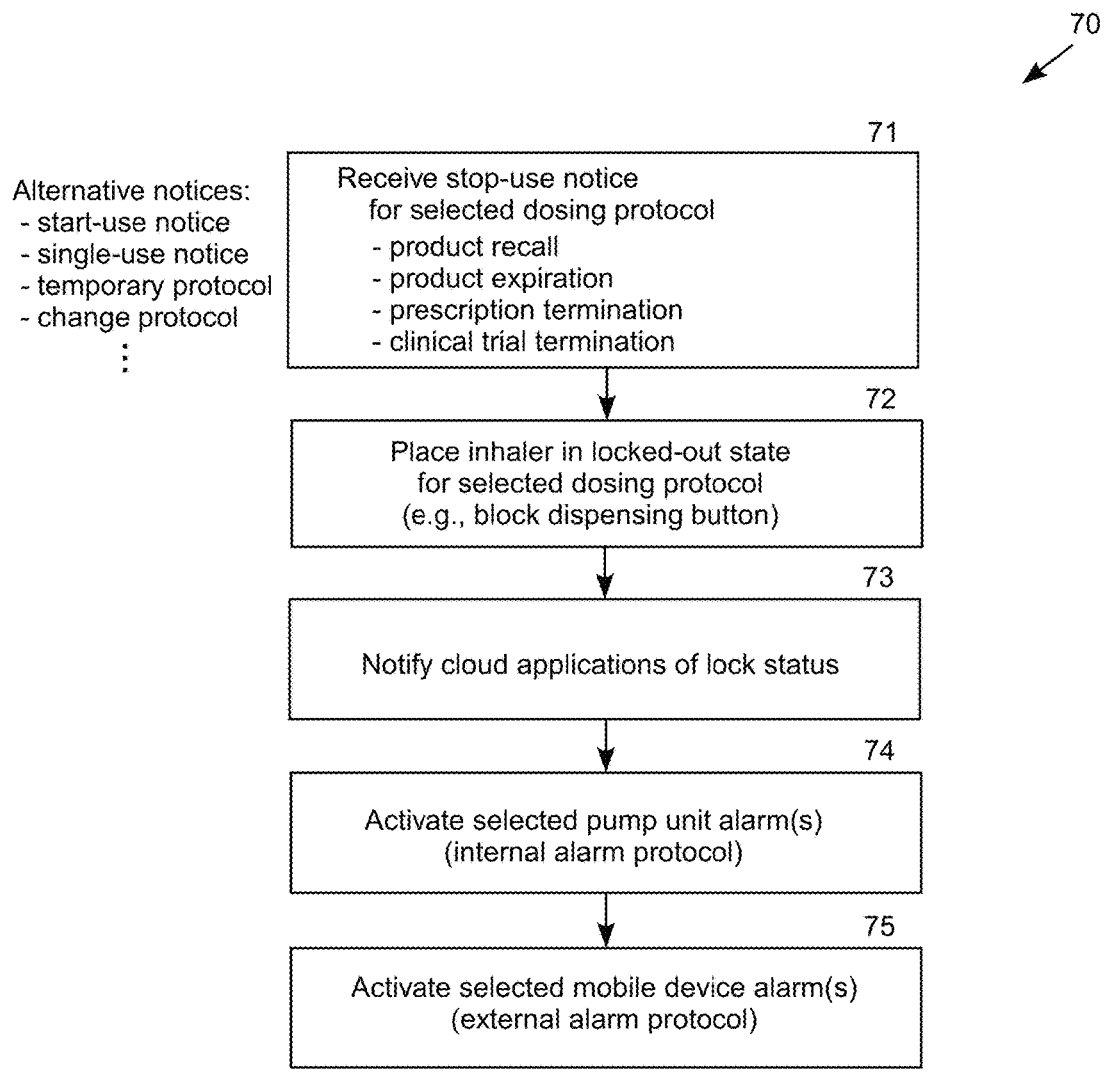
FIG. 7 is a logic flow diagram illustrating a procedure for placing the smart inhaler into a locked-out state and activating associated notifications and alarms.

FIG. 7 is a logic flow diagram illustrating a procedure 70 for placing the smart inhaler into a locked-out state and activating associated notifications and alarms. In step 71, the mobile app receives a stop-use notification for a selected dosing protocol. For example, stop-use notification may be received from the online system associated with the prescribing physician, clinical trial administrator, or the formulator of the product. The stop-use notification may be related to a product recall, expiration, prescription termination, or clinical trial termination. The mobile app may also receive and implement other types of notices over the cloud, such as a start-use notice, single-use notice, temporary protocol notice, change protocol notice, and so forth. The mobile app cloud connection thus provides a way to remotely control protocols and operation of the smart inhaler based on physician decisions, formulator decisions, health measurements received from ancillary devices, user feedback, lab test, clinical analysis, and so forth. To aid in these decisions, the mobile app may provide for a greater level of user feedback through multi-media and interactive feedback over the cloud, such as text chat, video chat, recorded feedback, email and other multi-media and interactive techniques to generate a richer data set to monitor side effects and ensure that the user is experiencing the desired result. Ancillary device measurements and user feedback, including multi-media and interactive feedback, can also be used as a safeguard to ensure that the only the authorized user is taking the product in accordance with the authorized protocol.

Step 71 is followed by step 72, in which the smart inhaler is locked-out for the selected dosing protocol, for example by blocking or disabling the dispensing button on the pump unit. In multi-protocol and multi-user embodiments, the smart inhaler can be locked-out on a per-cartridge and on a per-user basis. Step 72 is followed by step 73, in which the mobile app notifies cloud components, as appropriate, of the lock-out status. For example, the prescribing physician or clinical trial administrator may be notified of lock-outs ordered by a product formulator, and the product formulator may be notified of the successful lock-out for each specific canister subject to a product recall or expiration. Step 73 is followed by step 74, in which the pump unit activates an internal alarm protocol, and step 74 is followed by step 75 in which the mobile app activates an external alarm protocol, to notify the user of the lock-out status.

Figure 8:
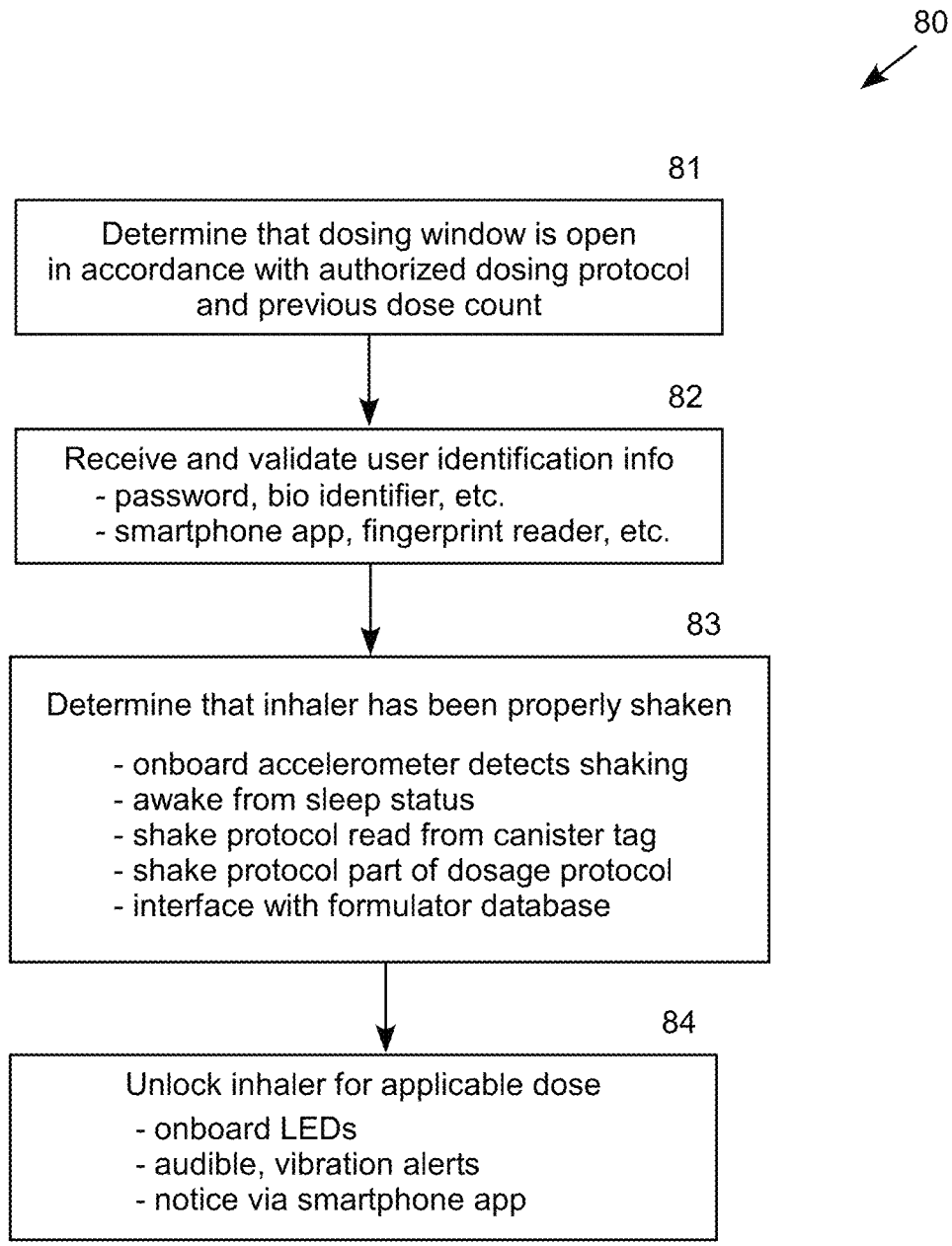
FIG. 8 is a logic flow diagram illustrating a procedure for unlocking the smart inhaler during a dosing window.

FIG. 8 is a logic flow diagram 80 illustrating a procedure for unlocking the smart inhaler for a dosing window. In step 81, the smart inhaler determines that a dosing window is open in accordance with an authorized dosing schedule and previous dose count. Opening of the dosing window is typically accompanied by internal and external notification protocols. Step 81 is followed by step 82, in which the smart inhaler receives and validates user identification information, such as a password, MMJ Registration Card number or bio-identifier (e.g. fingerprint, retina scan, photo, face scan, voice command). While the user identification information is typically received through the mobile app, the smart inhaler may be configured to receive certain types of user identification information (e.g., voice command) so that the smart inhaler can be activated for a dosing event even when connectivity does not exist between the mobile app and the smart inhaler.

Step 82 is followed by step 83, in which the smart inhaler determines whether the inhaler has been properly shaken. More specifically, the onboard accelerometer provides an acceleration signal to the microprocessor, which may awake from a sleep status and read a shake protocol from the on board memory. The shake protocol may be part of the cartridge information read from the memory, which is specific to the product in the canister. The shake protocol may also be downloaded from the cloud systems associates with the formulator the provider. As a result, the smart inhaler does not active for a dosing event until the inhaler has been properly shaken, which may be indicated by a change in the illumination or flashing state of the LED indicator or other suitable notification (e.g., beeping or voice notification "canister is adequately shaken"). Step 83 is followed by step 84, in which the smart inhaler is unlocked for the dosing event, which may be accompanied by its own internal and external notifications.

Figure 9:
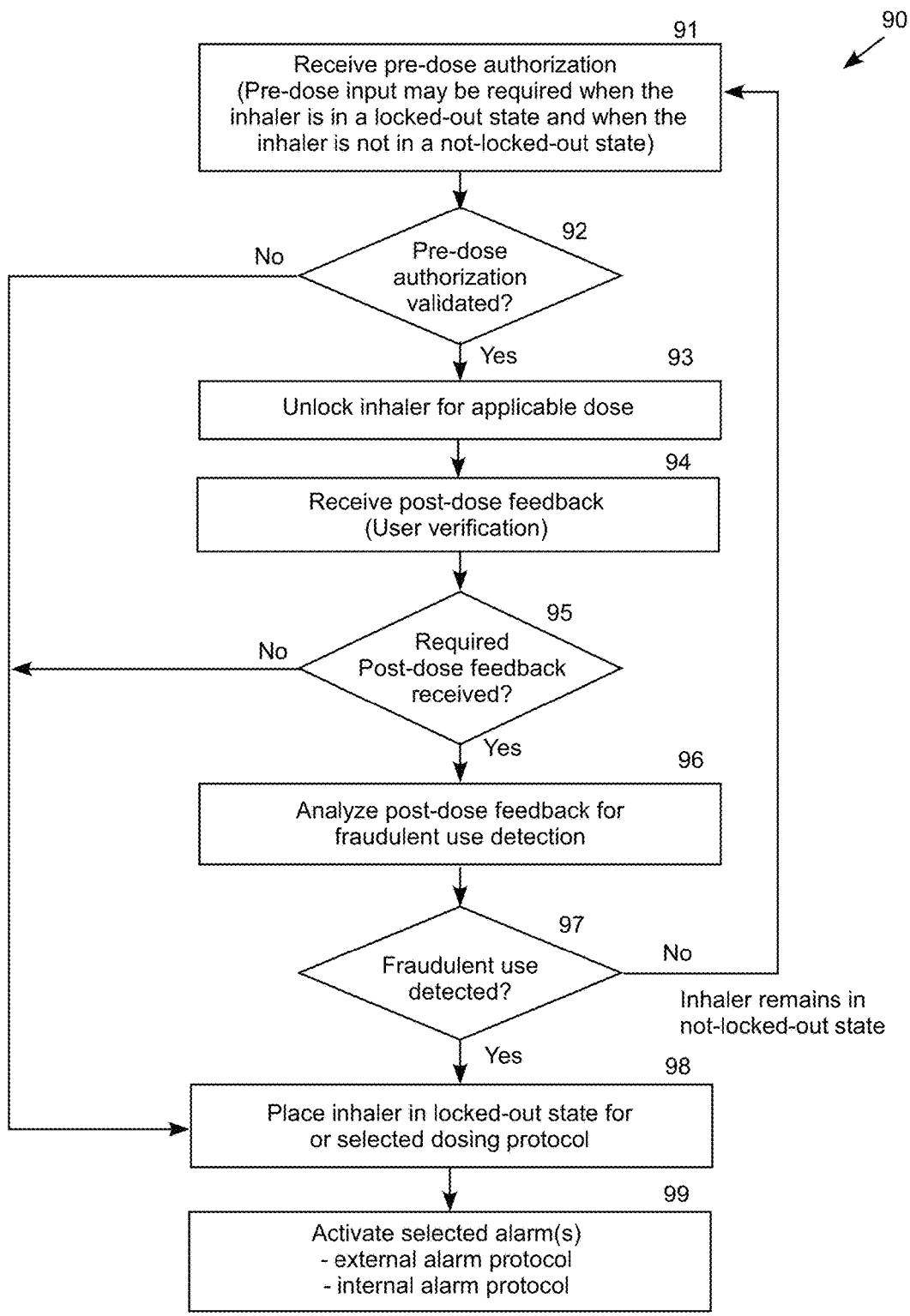
FIG. 9 is a logic flow diagram illustrating a security procedure implemented by the smart inhaler.

FIG. 9 is a logic flow diagram illustrating a security procedure 90 implemented by the smart inhaler system. In step 91, the smart inhaler receives pre-dose authorization from the user, which may be required when the inhaler is in a locked-out state and when the inhaler is not in a locked-out state. A variety of pre-dose authorization information may be required based on the desired level of security. For example, the pre-dose authorization information may include a password, MMJ Registration Card number, voice command, touch-screen gesture, and so forth. For additional security, the pre-dose authorization information may include a bio-identifier, such as a fingerprint, retina scan, photo or scan of the user's face, signature, voice recognition, or the like. A lower level of pre-dose authorization information may be required every time the smart inhaler is used, while a higher level may be required on a less frequent basis, such as weekly. A registered user's credentials acquired at the time of pre-dose authorization, such verified sources of identification and a photo of the user's face, may be compared against the user's verified credentials stored locally and/or in the cloud (e.g., Federated ID identity management). Although the smart inhaler usually receives the pre-dose authorization through the mobile app, there may be instances where the pre-dose authorization is received directly by the smart inhaler, for example when there is no connectivity between the user's smart inhaler and the user's mobile app. In addition, some embodiments may be configured to routinely receive the pre-dose authorization through the smart inhaler itself. For example, the smart inhaler may receive the pre-dose authorization through a photo of the user's face or voice command, which may involve voice recognition. In a multi-user embodiment, the pre-dose authorization may be required for a user registered to use the specific cartridge installed in the smart inhaler.

In general, pre-dose and post-dose verification and feedback requirements may be established on a per-cartridge basis. Although the verification procedures may be applied by the mobile app or the smart inhaler, or a combination, mobile app verification for an illustrative subject protocol is described below. Step 91 is followed by step 92, in which the mobile app determines whether the pre-dose authorization information is properly validated. If the pre-dose authorization information is not validated, the "no" branch is followed from step 92 to step 98, in which the smart inhaler is placed into a locked-out state for the subject protocol. If the pre-dose authorization information is validated, the "yes" branch is followed from step 92 to step 93, in which the inhaler is unlocked for the dosing event. After the dose has been administered, step 93 is followed by step 94, in which the mobile app should receive post-dose feedback. While required post-dose feedback is typically maintained by the mobile app 12 in accordance with settings information, the provider 15a or the formulator 18 may also establish post-dose feedback requirements or request specific post-dose feedback on a case-by-case basis. This typically involves a post-dose notification send from the provider 15a or the formulator 18 to the mobile app 12. User verification is typically required before the user can enter the post-dose feedback. In addition, multiple types of post-dose feedback may be required at one or more different times, such as dose confirmation immediately following the dosing event and feedback about how the user is feeling at a later time. For example, the user may be required to enter post-dose feedback in the morning to explain how well the user slept, how well the dose worked, how much pain the user experienced, other discomfort, and side effects the user may have experienced. The smart inhaler may remain locked until the correct type of post-dose feedback has been received. The post-dose feedback can therefore be used to monitor product efficacy, patient condition, and side effects on a per-dose basis, which can be very valuable for dose modification, monitoring disease (or other condition) progression, and clinical trial administration. Missing post-dose feedback may be used to detect fraudulent or other improper use of the inhaler. Post-dose feedback received, such as textual or photo feedback, can also be analyzed by the mobile app or cloud-based systems to detect fraudulent or other improper use of the inhaler. The smart inhaler system thus provides innovative opportunities for secure, per-dose monitoring of in-home, patient-administered medications (or other products) for monitoring disease (or other condition) progression, conducting clinical trials, developing new drugs, evaluating experimental drugs, and so forth.

Step 94 is followed by step 95, in which the mobile app determines whether the required post-dose feedback has been received. If the required post-dose feedback not has been received, the "no" branch is followed from step 95 to step 98, in which the smart inhaler is placed into a locked-out state for the subject protocol. If the required post-dose feedback has been received, the "yes" branch is followed from step 95 to step 96, in which the mobile app analyzes the post-dose feedback for fraud detection. This may include downloading information from one or more cloud platforms or uploading the post-dose feedback to one or more cloud platforms that conduct or participate in the analysis. Step 96 is followed by step 97, in which the mobile app determines whether fraudulent or other improper use of the smart inhaler has been detected. If fraudulent or other improper use of the smart inhaler has not been detected, the inhaler remains in a not-locked-out state for the selected protocol and the "no" branch is followed from step 97 back to step 91, in which the inhaler waits for another dosing event. If fraudulent or other improper use of the smart inhaler has been detected, the "yes" branch is followed from step 97 to step 98, in which the smart inhaler is placed into a locked-out state for the subject protocol. Step 97 is followed by step 98, in which the smart inhaler initiates an applicable internal alarm protocol and the mobile app initiates an applicable external alarm protocol for the locked-out condition.

Figure 10:
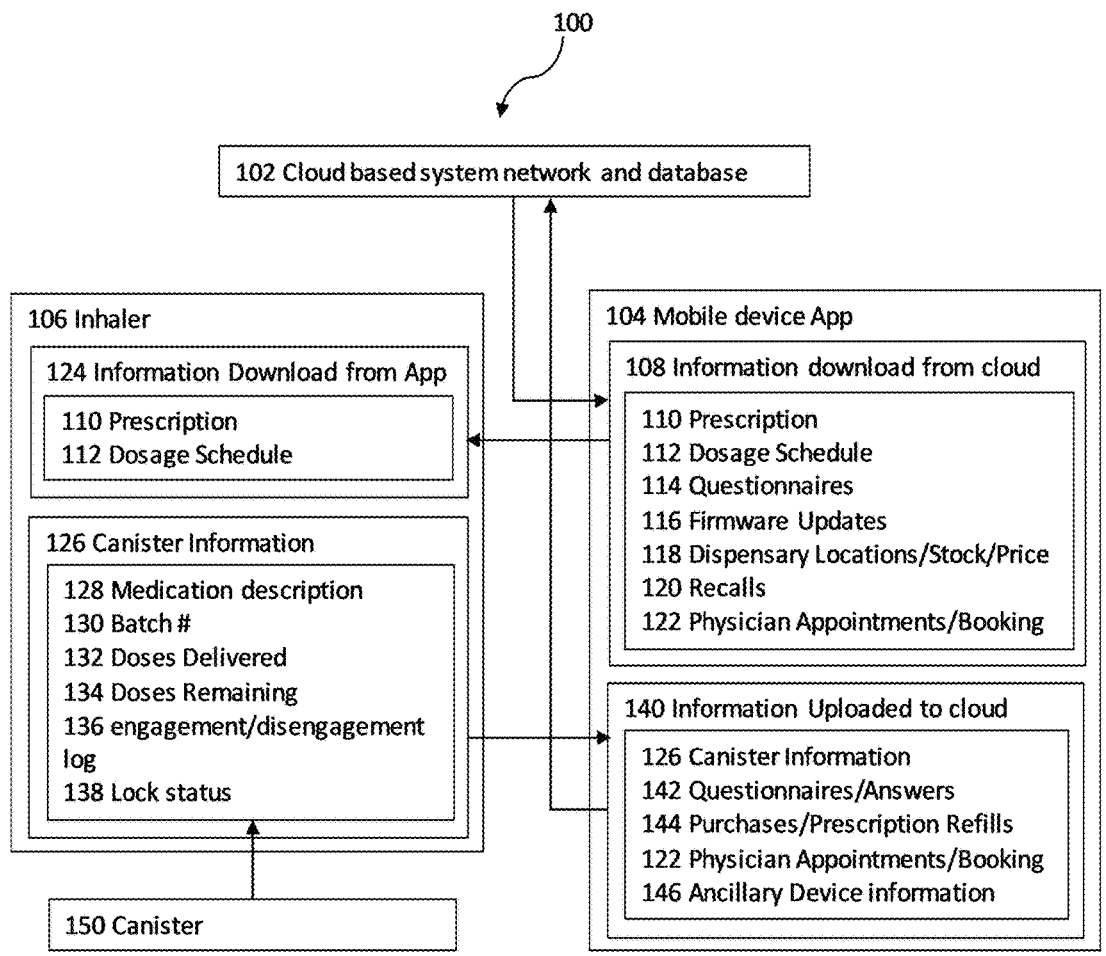
FIG. 10 is a block diagram illustrating information exchange between the smart inhaler, a mobile smart inhaler app, and a cloud-based system.
Figure 11:
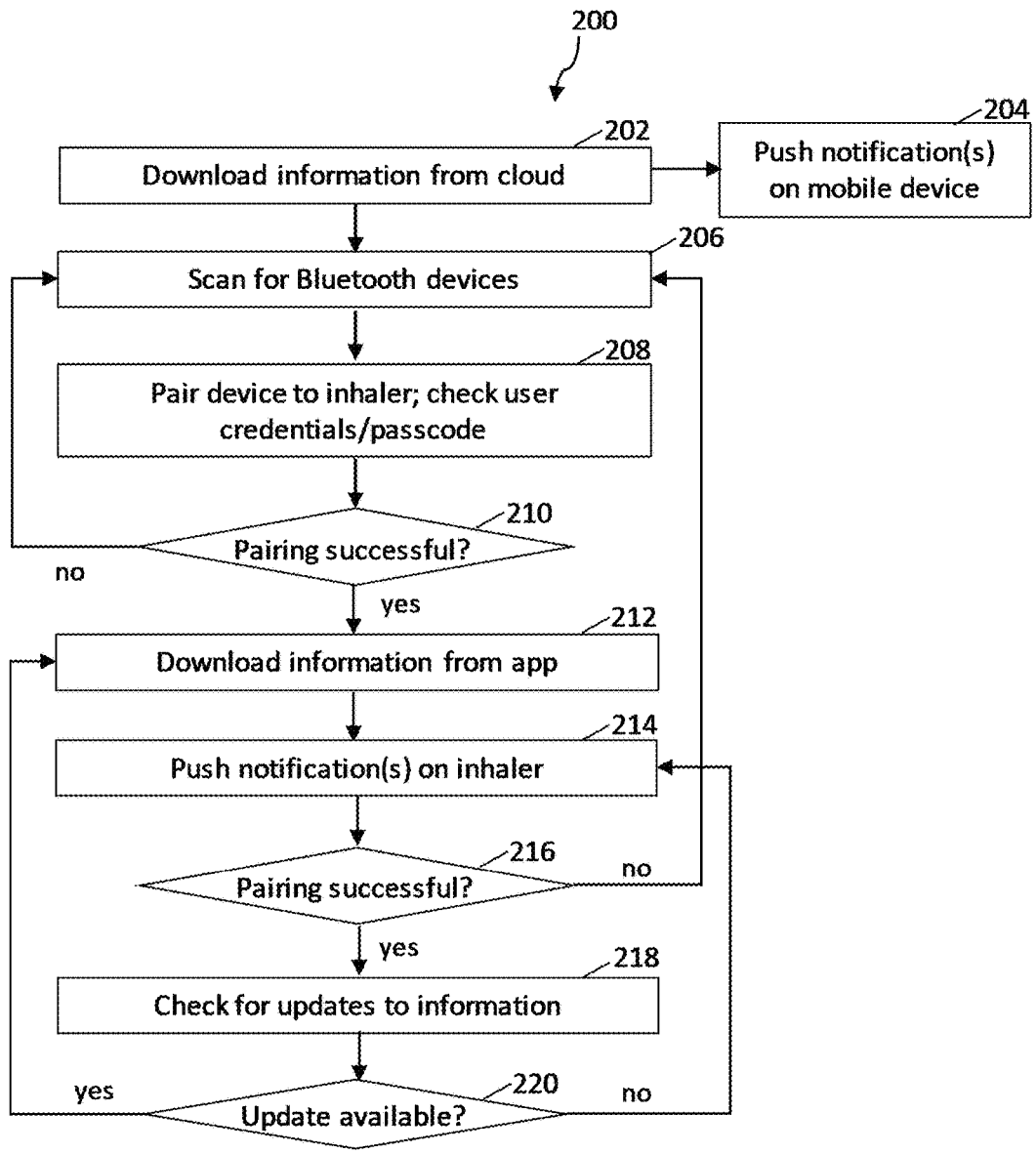
FIG. 11 is a logic flow diagram illustrating a procedure for downloading information from the cloud to the mobile app and the smart inhaler.
Figure 12:
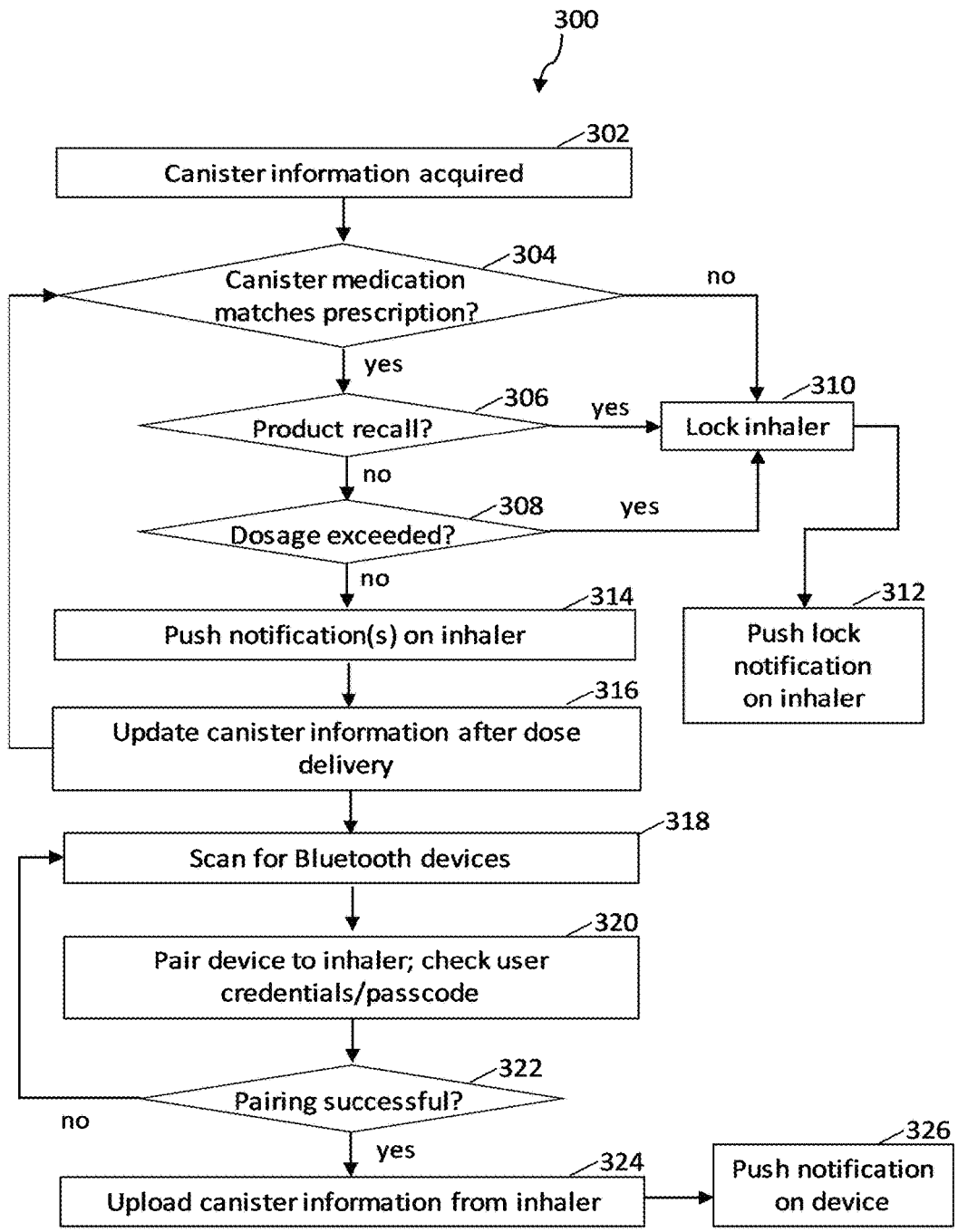
FIG. 12 is a logic flow diagram illustrating a procedure for uploading information from the smart inhaler to the mobile app and the cloud.

FIG. 10 is a block diagram illustrating information exchange 100 between smart metered-dose inhaler 106, the mobile app 104 running on the user's mobile device, and the cloud 102. FIG. 11 is a logic flow diagram illustrating a procedure 200 for downloading information from the cloud 102 to the mobile device app 104, and from the app to the inhaler 106. FIG. 12 is a logic flow diagram illustrating a procedure 300 for uploading information from the inhaler 106 to the app 104, and from the app to the cloud 102. The description of FIGS. 11 and 12, below, also refers to the components shown on FIG. 10, which illustrates one particular example information exchange 100 between the cloud 102, the mobile device app 104, and the inhaler 106.

Information 108 is downloaded from the cloud 102 by the app 104 via WIFI and/or mobile network connectivity. In this particular example, the information 108 includes a prescription 110, a dosage schedule 112, a questionnaires 114, firmware updates 116, dispensary details 118, recalls 120 and physician appointment and booking details 122. The information 108 may be updated on the cloud 102 and downloaded in real-time to the app 104 so long as WIFI and/or mobile network connectivity between the app 104 and the cloud 102 is maintained.

In addition, information 124 is typically downloaded from the app 104 to the inhaler 106 via a Bluetooth link. The information 124 includes a prescription 110 and a dosage schedule 112, which may be updated on the app 104 and downloaded in real-time to the inhaler 106 so long as Bluetooth connectivity is maintained between the app 104 and the inhaler 106. If Bluetooth connectivity is lost between the inhaler 106 and the app 104, the information 124 is stored on the inhaler until it is updated via download from the app 104 when Bluetooth connectivity is reestablished. This allows the inhaler 106 to continue to operate according to the dosage schedule 112 while connectivity is lost, and then push notifications to the app 104 when connectivity is reestablished between the inhaler 106 and app 104.

FIG. 11 illustrates a flow chart showing a method 200 for downloading information from the cloud to the mobile app and from the mobile app to the inhaler. As shown in FIG. 10, for example, the information 108 is downloaded from the cloud 102 to the app 104, and the information 124 is downloaded from the app 104 to the inhaler 106, in accordance with this particular embodiment. In step 202, the information 108 is downloaded from the cloud 102 to the mobile device app 104 over WIFI or mobile networks. Based on the information downloaded in step 202, step 202 may be followed by step 204, in which the app 104 may push notifications onto the mobile device (represented by the mobile device 12 shown in FIG. 1). For example, the information 108 may include a dosing schedule 112 shown in FIG. 10, and the notifications pushed onto the mobile device 12 may include visual, audible, and tactile notifications indicating that it is time for a dose to be administered through the inhaler in accordance with the dosing schedule. For example, the app 104 may cause the user's mobile device to vibrate, chime, and display a calendar notification when it is time to take a dose in accordance with the dosage schedule.

Step 202 is followed by step 206, in which the app 104 causes the user's mobile device to scan for Bluetooth devices in the vicinity of the mobile device. If the inhaler is within range of the mobile device, step 206 is followed by step 208, in which the mobile device compares the user's credentials stored by the app 104 against the credentials stored on the inhaler 106 to ensure that the mobile device is paired to the correct inhaler. This is a security measure requiring the particular inhaler to be registered to a particular mobile app installed on a particular mobile device, with this step ensuring that only the specific inhaler registered to operate with the specific mobile device can be paired the particular inhaler. For example, the user's inhaler 106 is registered to pair only the user's mobile device, as controlled by the mobile app 104 installed on the user's mobile device, when the inhaler is initially issued (and possibly prescribed by a physician) for use by that particular user. This may include receiving a passcode or bio-identifier (e.g., fingerprint, retina scan, face photo, face scan, voice command) associated with the user. Step 208 is followed by step 210, in which mobile device app 104 determines whether the user's inhaler 106 is successfully paired with the user's mobile device running the mobile device app 104. If the inhaler is not successfully paired with the mobile device, the "no" branch is followed back from step 210 to step 206, in which the mobile device continues to scan for Bluetooth devices in the vicinity of the mobile device. If the inhaler is successfully paired with the mobile device, the "yes" branch is followed from step 210 to step 212, in which information (such as information 124 in FIG. 10) is downloaded from the app 104 to the inhaler 106. Step 212 is followed by step 214, in which the inhaler 106 may push notifications onto the inhaler 106 based on the information downloaded in step 212. For example, if the information downloaded to the inhaler in step 212 includes a dosage schedule (such as dosage schedule 112 in FIG. 10), the notification pushed on the inhaler in step 214 may include displaying a notification on the inhaler. For example, inhaler 106 may activate notification devices (e.g., a flashing LED, tactile vibration, audible beep alarm, audible voice alarm, etc.) on the inhaler when it is time to take a dose.

Step 214 is followed by step 216, in which the app 104 routinely checks whether the user's inhaler 106 is still paired to the user's mobile device. If the inhaler is no longer paired with the mobile device, the "no" branch is followed back from step 216 to step 206, in which the mobile device scans for Bluetooth devices in the vicinity of the mobile device. If the inhaler remains paired with the mobile device, step 216 is followed by step 218, in which the app 104 checks the cloud 102 for updates to be downloaded (for example, updates to the information 108 shown in FIG. 10); and the inhaler 106 checks the app 104 for updates to be downloaded (for example, updates to the information 124 shown in FIG. 10) If updates are available, the "yes" branch is followed from step 220 to step 212, in which the updated are downloaded from the cloud 102 to the app 104 and/or from the app 104 to the inhaler 106. If there are no updates available, the "no" branch is followed from step 220 to step 214, in which the inhaler 106 continues to push notification in accordance with the dosage schedule. The type and frequency of the notification activated by the inhaler 106 and the app 104 may typically be controlled by the user through setting available in the app 104.

Referring again to FIG. 10, the inhaler 106 also acquires canister information 126 when a canister 150 containing medication is installed in the inhaler 106. The canister information 126 may be stored in a computer-readable format (represented by the cartridge memory 28 shown in FIG. 2B) that is physically located on the canister 150 or on the mouthpiece holding the canister. For example, the canister information 126 may be stored on an electronic tag located on the canister, such as a barcode, QR code, RFID tag, NFC chip or another suitable type of computer readable device or indicia. Additionally or alternatively, canister information 126 may be stored on an electronic tag located on the mouthpiece unit, which is typically attached to the mouthpiece unit when the canister is installed into the mouthpiece unit, for example at the formulator or dispensary. As another alternative, the canister information 126 may be stored in an electronic chip carried by the canister or the mouthpiece unit. As another option, a code (e.g., canister serial number) may be stored on the canister or mouthpiece, which the app 104 uploads and uses to look up (index) information stored by the app or in the cloud. For example, the app 104 may use the code stored with the canister to download a portion of the canister information from the formulator's website (e.g., chemical contents of the canister, packaging date, expiration date) and from a physician's website (e.g., dosing schedule). In this particular example, the canister information 126 is encoded as a barcode on the canister 150 or the mouthpiece unit. The inhaler 106 includes a canister memory reader (represented by the cartridge memory reader 29 shown in FIG. 2B). In this example, the canister memory reader is a barcode reader that decodes the barcode on the canister 150 to obtain the canister information 126. In this particular embodiment, the canister information 126 includes a medication (or other contents) quantity and description 128, and a batch number 130. The inhaler updates the canister information along with dose utilization information as the canister is used, such as doses delivered 132, doses remaining 134, logging of the engagement and disengagement of the canister 136, and a lock status 138.

In this particular embodiment, the inhaler 106 compares the prescription 110 (downloaded from the cloud, for example from the prescribing physician's website) to the medication description 128 carried on the canister or mouthpiece, which may be issued separately from the inhaler pump unit (for example by a dispensary) to determine if there is a match. If the prescription 110 matches the medication 128 in the canister, the lock 138 is disengaged allowing the inhaler to dispense according to the dosage schedule 112. If the prescription 110 does not match the medication 128, the lock 138 is engaged to prevent the inhaler 106 from dispensing.

Following the delivery of a dose, the inhaler updates the canister information 126 including the doses delivered 132 and doses remaining 134. The updated canister information 126 is uploaded from the inhaler 106 to the app 104 via Bluetooth connectivity. The upload from the inhaler 106 to the app 104 occurs in real-time if Bluetooth connectivity is available between the user's inhaler and the user's mobile device. Alternatively, if Bluetooth connectivity is not available at the time of dose administration, the canister information 126 is uploaded at a later time when Bluetooth connectivity reestablished. This allows the inhaler 106 to push notifications to the app 104, such as doses remaining 134, when connectivity between is reestablished between the inhaler 106 and app 104. The app 104 then uploads information 140 (including the updated canister information 126 received from the inhaler 106) to the cloud 102 via WIFI and/or mobile network connectivity. This information 140 may also include answers to questionnaires 142 (such as post-dosage feedback), purchases 144, and ancillary device information 146. Again, the app 104 uploads the updates to the cloud 102 in real-time if communication connectivity is available between the user's mobile device and the cloud. Alternatively, if connectivity is not available when the app receives an update from the inhaler, the canister information 126 is uploaded at a later time when communication connectivity reestablished. It should be noted that additional post-dose feedback may be received from the user and uploaded to the cloud at one or more specified times after dose administration, such one hour later, at the time of expected medication onset, at bed time or in the morning. This additional reporting provides a safety mechanism for fraud detection as well as a richer information set for assessing the effectiveness and side effects of the product administered by the inhaler on a per-dose basis. This higher level of user feedback may be particularly advantageous when the inhaler is used for controlled substances, clinical trials, addiction treatment, judicial supervision, cases of prior inhaler misuse, acute care, higher-risk settings (e.g., foster care, hospice) and other situations that justify heightened reporting requirements.

FIG. 12 is a flow chart showing a method 300 for uploading information from an inhaler to a mobile device app, and from the mobile app to the cloud, in accordance with an embodiment. In step 302, the inhaler pump unit acquires information (such as canister information 126 from canister 150 in FIG. 10) from the cartridge, for example by reading an electronic tag or chip carrier on the canister or the mouthpiece carrying the canister. The cartridge information is typically acquired when the cartridge is installed into the pump unit and is updated whenever the canister is used. The pump unit also uploads the canister information to the mobile app running on the mobile device registered to work with the inhaler and a series of checks. For example, step 302 is followed by step 304, in which the mobile app compares the medication description 128 acquired from the canister to the prescription 110 downloaded from the cloud for the user registered to use the inhaler. If the medication description does not match the prescription, the "no" branch is followed from step 302 to step 310, in which the mobile app 104 instructs the inhaler 106 to lock the inhaler, and the inhaler does so for example by moving an abutment to physically block depression of the dispensing button. Step 310 is followed by step 312, in which the app and inhaler activate associated alarms and notifications. For example, the inhaler and the mobile app may also display or play one or more "lock-out" notifications, such as a blaring alarm. The app may also send a communication to one or more designated third parties, such as the user's physician, parent, care taker or authorities to report an apparent attempt to misuse the inhaler. Additional steps may be required to reactivate the inhaler and distinguish between an accidental mix-up and fraudulent attempt to misuse the inhaler.

If the prescription matches the medication contents, the "yes" branch is followed from step 304 to step 306, in which the app checks for a product recall, prescription change, authorization change or other factor indicating that inhaler should not be used to administer the product in the canister. This may include checking or downloading information from multiple cloud locations, such as websites associated with the formulator, provider, clinical trial monitor, guardian, facility (e.g., hospice) manager, caseworker, parole officer, judicial supervisor, offender database, and so forth. If there is a product recall or other information indicating that the contents of the canister should not be administered, the "yes" branch is followed from step 306 to step 310, in which the app places the inhaler in a locked-out state for the applicable cartridge, typically by blocking the dispensing button. If there is no product recall or other information indicating that the contents of the canister should not be administered, the "no" branch is followed from step 306 to step 308, in which the mobile app determines whether the authorized doses (or dosage) have been reached or exceeded, typically by checking the prescription against the updated canister information reflecting prior dose administration from the canister. If the authorized doses (or dosage) have been reached, the "yes" branch is followed from step 306 to step 310, in which the app places the inhaler in a locked-out condition for the applicable cartridge, typically by blocking the dispensing button. If the authorized doses (or dosage) have not been reached, the "no" branch is followed from step 308 to step 314, in which the inhaler and the mobile app activate notifications to alert the user that a dosing window is open (dose scheduled). The inhaler then allows the dispensing button on the inhaler to be depressed only enough times (and may also restrict the depth of depression of the button) to allow the user to take the scheduled quantity.

Following administration of the scheduled dose, step 314 is followed by step 316, in which the inhaler updates the canister information to reflect this dose, which is uploaded to the app. The upload occurs in real-time if there is connectivity between the inhaler and the app. Alternatively, if there is no connectivity at the time of dose administration, the upload occurs when connectivity is reestablished. Similarly, the app may upload information reflecting dose administration to the cloud, where it is received and reviewed by authorized personnel or systems. In this particular embodiment, step 316 may be followed by step 318, in which the inhaler scans for Bluetooth devices. If a mobile device is located within pairing range, step 318 is followed by step 320, in which the inhaler pairs with the mobile device and checks the credentials of the inhaler against the credentials to ensure that the user's inhaler only pairs with user's mobile device, which it is registered to work with. This may include receiving a passcode or bio-identifier (e.g., fingerprint, retina scan) associated with the user and other security checks. If the credentials and other security checks are confirmed, step 320 is followed by step 322, in which the inhaler determines whether it is paired with the user's mobile device. If the inhaler is not paired with the user's mobile device, the "no" branch is followed back to step 318, in which the inhaler scans for Bluetooth devices, which may include attempting to pair with another mobile device within pairing range. If the inhaler is not paired with the user's mobile device, the "yes" branch is followed to step 324, in which the inhaler canister information update is uploaded from the inhaler to the mobile app. The inhaler canister information update may also be uploaded from the mobile app to the cloud. Step 324 is followed by step 326, in which the user's mobile device (as controlled by the mobile app) and the inhaler activate notifications indicating that the scheduled dose has been taken and recorded.

Figure 13:
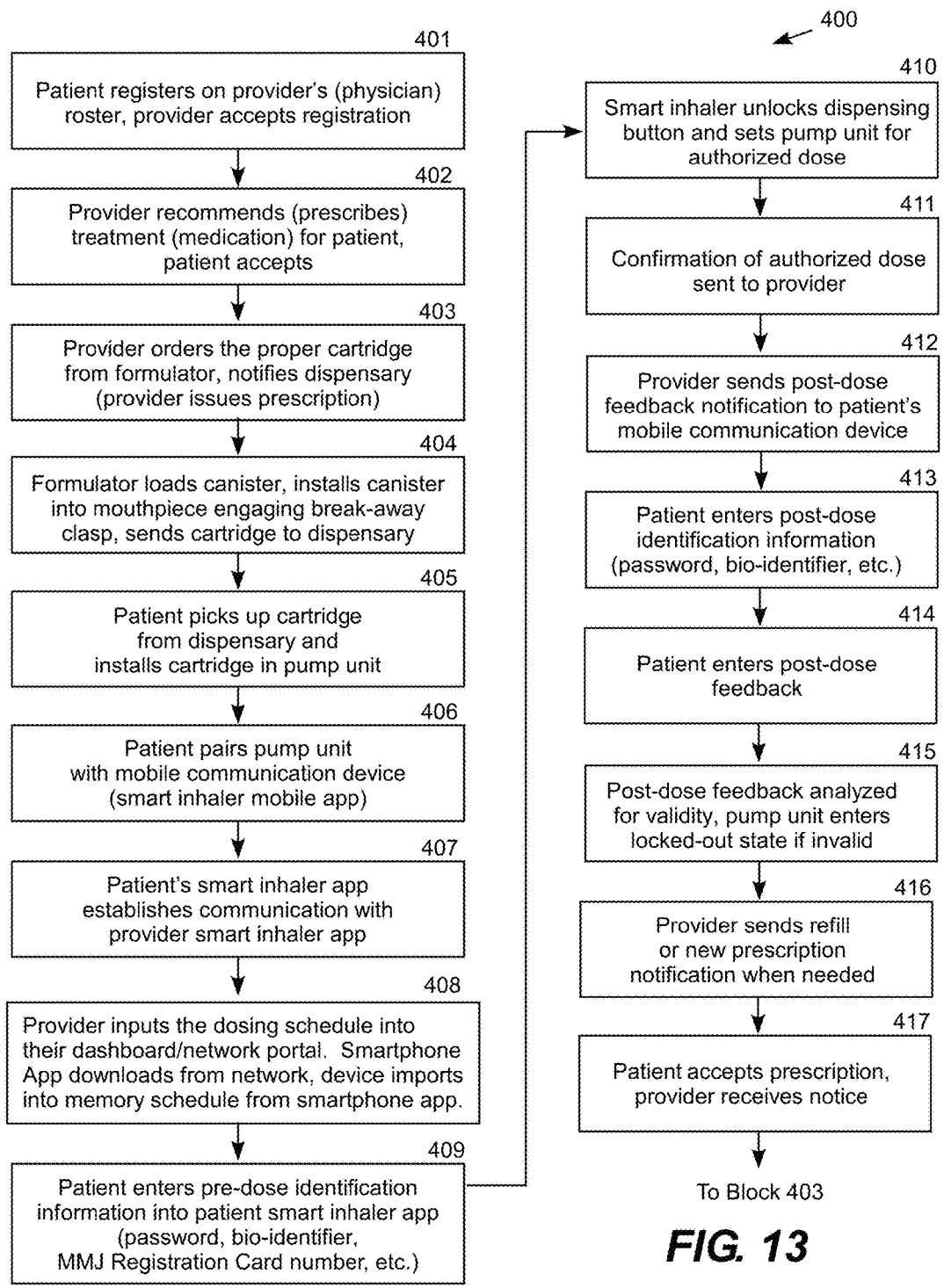
FIG. 13 is a logic flow diagram illustrating a procedure integrating the smart inhaler with the mobile app and other platforms over the cloud.

FIG. 13 is a logic flow diagram illustrating a procedure 400 integrating the smart inhaler with the mobile app and components of the cloud. The following description will also make reference to the smart inhaler system 10 shown in FIG. 1. While the procedure is applicable to clinical trial participants and other users of the smart inhaler, this particular example will refer to a patient (user) and provider (physician). In step 401, the patient registers on the patient roster on the provider system 15a, which the provider accepts. Step 401 is followed by step 402, in which provider recommends or prescribes a treatment or medication for the patient, which the patient accepts. Step 402 is followed by step 403, in which the provider issues the prescription 15b typically by ordering a cartridge with a pressurized canister containing the prescribed medication from the formulator 18 for delivery to a dispensary 15c selected by the user. The provider system 15a also notifies the dispensary 15c to expect and prepare for the delivery. Step 403 is followed by step 404, in which the formulator 18 manufactures the prescribed cartridge 11b by loading a canister with the prescribed medication, installing the canister into a mouthpiece unit (engaging the single-use clasp in the mouthpiece unit), and sending the cartridge 11b to the dispensary 15c. Step 404 is followed by step 405, in which the patient receives the cartridge 11b from the dispensary 15c and installs the cartridge into the pump unit 11a.

To activate the smart inhaler 11, step 405 is followed by step 406, in which the patient pairs the microprocessor 11c in the pump unit 11a with the smart inhaler mobile app 12 running on the user's mobile device, typically a smartphone. (See FIG. 11). Step 406 is followed by step 407, in which the mobile app 12 establishes communications with the provider system 15a. Step 407 is followed by step 408, in which the provider 15a sends a dosing schedule for the cartridge 11b to the patient, for example through a communication between the provider's mobile app 16 and the patient's mobile app 12. In the particular embodiment, for example, the Provider inputs the dosing schedule into the dashboard or network portal of the provider system 15a, which downloads the dosing schedule to the Provider's mobile app 16. The user's mobile app 12 then downloads the dosing schedule from Provider's mobile app 16 over the cloud 17. The user's mobile app 12 then downloads the dosing schedule to the memory 11d of the smart inhaler 11. Step 408 is followed by step 409, in which the patient enters pre-dose identification information into the patient's mobile app 12, or in some cases into the smart inhaler 11 directly (See FIG. 9). Step 409 is followed by step 410, in which the smart inhaler 11 unlocks for the authorized dosing event, typically for a specified number of puffs (pumps of the dispensing button).

After the user takes the authorized dose, the inhaler 11 automatically locks and step 410 is followed by step 411, in which the inhaler 11 uploads a dose confirmation to the patient's mobile app 12, which uploads the dose confirmation to the provider's mobile app 16, which may further upload the dose confirmation to the formulator 18. Step 411 is followed by step 412, in which the formulator 18 or the provider 15a, typically through the mobile app 16, may send a post-dose notification to the patient's mobile app 12. Step 412 is followed by step 413, in which the user enters identification information, which is validated by the mobile app 12 (see FIG. 9). Step 413 is followed by step 414, in which the user enters post-dose feedback (see FIGS. 14-17). Step 414 is followed by step 415, in which the inhaler 11 may enter a locked-out state if the required post-dose feedback is not received, or if analysis of the post-dose feedback indicated that the inhaler has been used (or may have been used) fraudulently or improperly (see FIG. 9).

The smart inhaler system 10 can also be used to order and fill new prescriptions and refill prescription. This is represented by step 416, in which the provider mobile app 16 sends a new prescription or refill notification to the patient's mobile app 12. Step 416 is followed by step 417, in which the patient accepts the prescription, which is communicated through a refill acceptance notice sent from the patient's mobile app 12 to the provider's mobile app 16. This may be accompanied by a "stop-use order" for the previous cartridge 11b if there are doses remaining that should not be taken by the patient (see FIG. 7). Routine 400 then loops back to step 403, in which the prescription is ordered, filled and picked up by the patient.

Figure 14:
FIG. 14 is a conceptual illustration of a user interface displayed by the mobile app showing a dosing schedule.

FIG. 14 is a conceptual illustration of a user interface 1400 displayed by the mobile app showing a dosing schedule. The dosing schedule shows the associated product, in this example "Alprazolam," the date and time of the scheduled dosing events, the quantity to be administered, and the doses remaining after the dosing event. In this example, the quantity "2 puffs" instructs the user to press the dispensing button twice for each dosing event, after which the dispensing button is automatically locked. An associated "doses taken" schedule can also be displayed to show the doses previously taken by the user. In multi-cartridge and multi-user embodiments, the dosing schedules are made available on a per-cartridge and per-user basis. The dosing schedule 1400 also displays a "settings" icon that the user (or other authorized person) can select to initiate a variety of menu-driven configuration panels. The configurable features of the system, which can typically be set on a per-cartridge and per-user basis, include items such as the elements required for user identification (e.g., password, MMJ Registration Card number, face photo, fingerprint, etc.), post-dose feedback, internal alarm protocols performed by the smart inhaler, external alarm protocols performed by the smart inhaler, network addresses of associated cloud platforms, and so forth.

Figure 15:
FIG. 15 is a conceptual illustration of a first user interface for a questionnaire displayed by the mobile app for receiving user feedback.
Figure 16:
FIG. 16 is a conceptual illustration of a second user interface for the questionnaire.

FIG. 15 and FIG. 16 are conceptual illustrations of two user interfaces 1500 and 1600 displayed by the mobile app for receiving post-dose user feedback. These user interfaces show two representative questions of a radio-button questionnaire that the user may be required to complete. User interface 1500 allows the user to answer "yes" or "no" to the question "Did you experience any abdominal pain during the night?" User interface 1600 allows the user to select a radio button indicating the duration of the pain. In general, the questionnaires can be supplied on a per-cartridge basis and may be part of the canister information stored in the cartridge memory supplied with each cartridge. The questionnaire may also be updated or modified over the cloud based on the needs of individual users (e.g., children, elderly patients, patients with progressive conditions, etc.) and protocols (e.g., clinical trial administration, experimental medication or other product evaluation, etc.).

FIG. 17 is a conceptual illustration of a user interface 1700 displayed by the mobile app for receiving multi-media and interactive user feedback. This user interface 1700 shows a third question of the questionnaire using a slider to indicate a level of pain experienced along with a text box 1701 allowing the user to enter a textual response to the question "Describe in your own words how you are feeling, any recent changes, and how well you believe the treatment is working." The user interface 1700 also displays a number of icons 1702a-1702n that the user can select to enter various types of multi-media and interactive feedback. For example, the icon 1702a may be selected to allow the user to attach a picture taken with the camera on the user's mobile device, the icon 1702b may be selected to allow the user to attach a video taken with the camera and microphone on the user's mobile device, the icon 1702c may be selected to allow the user to attach a file, the icon 1702n may be selected to allow the user to initiate a chat or video chat session, and so forth. These features are particularly helpful for conversing with the user's physician or clinical trial administrator. For example, a picture of a skin rash or wound, a video of the user experiencing sleep apnea, or photo of the user's face for security identification can be attached and uploaded for review by the user's physician, clinical trial administrator, the formulator of the product in the subject cartridge, or an artificial intelligence platform. The user's vital signs and other measurements taken by ancillary devices can also be uploaded from the user's mobile app for review along with other clinical test results obtained from third-parties (e.g., lab tests, MRI results, etc.). The user can then initiate a text or video chat session to discuss these multi-media materials with the user's physician or clinical trial administrator. The system 10 consolidates all of the relevant information in an single platform to facilitate the conversation. Based on all of these materials and interactive patient interviews, the physician or clinical trial administrator can take appropriate actions, such as changing the dosing schedule, ordering a new cartridge, or entering a "stop-use order" for the relevant cartridge, which are automatically downloaded to the user's mobile app and on to the user's smart inhaler.

It will therefore be appreciated that the illustrative embodiments shown in the figures include an electronic metered-dose smart inhaler, mobile app, and cloud-based software system that validates users and inhaler use protocols (e.g., medical prescriptions, clinical trial regimens, experimental drug regimens), controls and monitors per-dose usage, captures efficacy results and feedback from medical cannabis (marijuana) patients for review and input by prescribing physicians, medicine formulators and artificial intelligence. Conventional cannabis delivery methods fail to provide the ability for patient, physician and formulator interaction using per-dose administration and feedback data. This communication loop is critical to ensure that physician recommendations and specific prescribed formulations are beneficial to the treatment of the patients ailment.

Medicine effectiveness data and patient symptom feedback is severely delayed to the physician and to the formulator. Patient feedback needs to occur in real-time so that a treatment regime can be adjusted to meet patient needs as quickly as possible between doctor's office visits which typically take place every 90 days.

Protocol administrators, such as physicians and clinical trial operators, using conventional cannabis medicine administration and monitoring systems are unable to make critical early adjustments to patient's regimen due to the time lag in understanding the initial and early effects on the patient. Conventional cannabis systems also fail to provide physicians with a reference database to assist decisions they make on recommending the most effective medicine produced by the best formulator to their patients. Formulators can also benefit from understanding how their medicines are affecting patient ailments and whether formulation adjustments need to be made to specific medicines to increase the efficacy for targeted ailments. Currently there are no existing device systems that allow formulators to gather useful data from patients that help guide in adjusting their medicines to increase the benefits of their medicine product offering.

The smart inhaler system provides systems and methods for collecting and organizing per-dose, typically real-time user feedback that is accessible to physicians, formulators, artificial intelligence, and other research and analysis systems and practitioners The smart inhaler and associated mobile app gather patient (and other user) inhaler use data and allows for user input regarding effectiveness of a protocol administered by the smart inhaler, such as a treatment regime for clinical trial or prescribed medication. This information is gathered and stored on a centralized network server where physicians, formulators, researchers and other practitioners can analyze the data to better understand if and when adjustments in protocol or formulation are necessary. The smart inhaler system thus creates a critical loop of communication to improve treatment efficacy by eliminating any delay of information provided by the patient.

The smart inhaler system incorporates multiple sources and methods in the gathering of relevant data and perform analytics regarding the patient's inhaler use, physical status and medical condition. The system incorporates vitals gathered from ancillary and add-on components that capture data, such as but not limited to, patient heart rate, blood pressure, body temperature, respiration rate, glucose monitoring, blood oxygen level, sleep patterns, exercise/activity patterns and weight monitoring. The device system will incorporate all forms of data, feedback and information into the patient's account folder on the system network for review by the physician and formulator. The device system software will also incorporate artificial intelligence (AI) that will analyze and process the patient data in order to provide predictive modeling and make recommendations in regards to potential patient treatment regimes, adjustments in dosing and formulations to increase efficacy and increase assurance in Physicians and Formulators that the proper treatment is being provided to the patient. Physicians may also upload patient clinical test data to the device system to increase the accuracy of the AI analytics. This clinical test data may include but is not limited to, blood test data, cardiovascular test data, MRI/CAT scan test data, and genome test data.

Physicians may use the AI results and per-dose, typically real-time data collected by the smart inhaler system to make instant modifications to the patient's dispensing amount and the frequency of the dispensing to improve treatment outcomes. The access to real-time data also allows the physician to monitor the dispensing device use and confirm if the patient is adhering to the prescribed regimen. The centralized information database created by the smart inhaler system will allow physicians to access patient and AI input and determine which formulators are producing the medicines with the highest efficacy rates and allow physicians to make a recommendation based on accurate data instead of making a random decision in selecting a medicine. Providing real-time patient feedback that is accessible to the formulators and incorporating AI results is invaluable in ensuring their medicines are compounded to target specific ailments. This user feedback and AI data allows the formulator to determine adjustments that are required to eliminate unwanted side effects of a medicine. There are no current methods or database resources for formulators to understand how their medicines are benefiting or negatively affecting users. The smart inhaler system will allow formulators to analyze user data, incorporate AI recommendations and make necessary changes to optimize and improve their medicines. The device in combination with the network software will allow formulators and physicians a very quick and efficient product recall capability in the event that a medicine needs to be recalled. The formulator can issue an electronic recall notice that will lock-out further use of the device utilizing the medicine to be recalled. Detailed electronic messaging can be sent to patients and doctors notifying them of the recall event.

The smart inhaler is a battery powered hand-held device that is slightly larger than a traditional inhaler product. It is familiar in appearance to a traditional inhaler with regards to the mouthpiece where the medicine is dispensed. The smart inhaler has a reusable main upper housing that provides an enclosure for the electronic components. The larger size is directly related to the space required for housing the device electronics and power supply. The device has as an internal PCB with a microprocessor, Bluetooth chip set, NFC antenna and/or RFID reader, battery charging circuitry, rechargeable battery, LED status indicators and other surface mounted components for completing the electronic system design. The device will connect to a smartphone and/or tablet to communicate with the software application. The device will incorporate electronic features and functions such as but not limited to; detection of dispensing events, preprogrammed dispensing event times, data log of dispensing events, alerts and notifications of dispensing events, visual/tactile/audible device status indicators, low power consumption/sleep mode and an accelerometer. The device may or may not have a power "On/Off" switch and may or may not always remain in a state of "On, Standby or Sleep mode". The software also has the capability to gather and aggregate information from third party smart devices such as Fitbit®, Apple Watch®, Garmin® watches and other smart information gathering devices. The information gives additional channels of information to the physician such as heart rate, sleep patterns, activity levels that can be combined with the patient's real-time feedback to develop a holistic understanding of how the treatment plan is working for the patient.

The smart inhaler has a removable and disposable lower housing that incorporates the valve stem, valve and jet features for properly dispensing the MDI canister medicine, a mouthpiece where the medicine exits the housing and a mating feature to secure the MDI canister into the lower housing. In traditional inhalers, the MDI canister is inserted from the top of the actuator. The smart inhaler differs in this and the MDI canister is attached to the lower housing and the assembly is inserted into the bottom of the device. The lower housing is removable and replaceable to the upper housing by means of a snap-fit feature. This feature engages with the pump unit (also called the "upper housing") by aligning and pressing the lower housing (also referred to as the or "mouthpiece unit" or "cartridge" when the mouthpiece unit is carrying a canister) into position. The lower housing may be disengaged and removed by pressing side tabs to release the snap-fit allowing the two parts to separate and pull apart the housings. The lower housing of the smart inhaler also has a feature that secures the MDI canister into the housing by means of a permanent snap fit. This feature allows the canister to be pressed into the lower housing for dispensing until the canister contents are depleted. The empty canister and lower housing are both discarded and a new canister/lower housing assembly can be installed into the upper housing. When the canister has been permanently secured into the lower housing and subsequently and forcefully removed from the lower housing, the permanent snap feature that secures the canister will be deformed and/or destroyed to the extent that the canister cannot be installed into the lower housing to be reused. This feature is to ensure that the lower housing is discarded after the canister contents are depleted for sanitary purposes and also to prevent other manufacturer's canisters from being inserted into the lower housing and reused ion the smart inhaler. The lower housing assembly is equipped with on-board memory storage that is capable of storing and containing information such as, but not limited to, canister contents, contents manufacturer, manufactured date, lot number, batch number, expiration date, etc. The memory component may be incorporated into the lower housing, lower housing assembly or the MDI canister. When the lower housing assembly is inserted into the upper housing, the upper housing PCB is equipped with a component to wirelessly read the data stored on the lower housing. The upper housing detects the installation of the lower housing, collects the information from the lower assembly and ports this data wirelessly to the smartphone app. The information can be viewed by the user on the smartphone app and viewed by the physician and formulator on the central network. Each time the lower housing is removed or inserted, the device will log this event. If a lower assembly with medicine "A" is inserted and dispensing events occur, the device will record and store these events to track consumption for that specific medicine. When medicine "A" is reinserted the device will resume counting dispensing events for Medicine "A" and continue counting until the canister is depleted. As the lower housing assembly with Medicine "A" approaches depletion, approximately 100 dispensing events, the device will send a notification to the smartphone app and alert the patient and/or physician that the MDI canister is almost empty. This advance notification allows the patient to ensure they have an immediate refill on-hand to replace the depleted canister or allows them the time to contact the physician for a prescription refill if required. The device app and software can automatically notify the prescribing physician that the patient's prescription is almost empty. The patient can then directly request a prescription refill by using the smartphone app. This system feature avoids patients from having to spend the extra money for an office visit with their doctor and also avoids the time required for this visit. In turn, the physician can review the patients adherence and feedback using the online system network to ensure the patient is progressing satisfactorily prior to authorizing the prescription refill. Once approved by the physician, the prescription is automatically send to the patient's dispensary and a message is sent to the patient when the prescription is ready for pick up. The physician can also reject the refill request and instruct the patient to schedule an in office visit for an evaluation.

The reusable upper housing of the device has a integrated dispensing button that interfaces with the canister when the lower assembly is installed. With traditional inhalers, the patient presses down on the actual canister to dispense, whereas in the smart inhaler, the user will press down on the dispensing button that forces the canister down in order to dispense. The upper housing has an internal function that can be controlled to allow the button to be pressed down or prevent the button from being pressed down to avoid accidental or unauthorized dispensing. A mechanical feature will engage with the dispensing button to create an interference of the up and down movement of the button and essentially positioning the button in a state of non-function. This function is controlled electronically via commands sent from the system application installed on a smartphone. The device and/or app can be programmed for individual dispensing events. When the dispensing event approaches, the button engagement feature will disengage allowing the user to dispense a pre-set amount. When the dispensing is completed the button engagement feature will reengage the button to prevent dispensing. There may be a preprogrammed window of time allowing the patient to dispense the medicine at their convenience. For example, the time to dispense is set for 3:00 PM, the device would disengage the dispensing button at 2:30 PM and remain disengaged until 3:30 PM, allowing the patient to take their medicine anytime within the 1 hour window. At 3:31 the dispensing button would be re-engaged to prevent the dispensing event until the next programmed event. The device app may or may not allow the user to override the dispensing button engagement by entering a passcode to disengage the button during times other that the preprogrammed dispensing events. For example, the patient realizes at 3:45 PM that the preprogrammed dispensing event was overlooked, a password code can be entered to immediately disengage the dispensing button for a short period, approximately 1-3 minutes, allowing the patient to take the previously overlook dispensing event. When a pre-programmed dispensing event is approaching, a notification will be activated. This notification may be in the form of an audible, visual and/or tactile (vibration) alert. The notification may also be in the form of an email, text or in-app alert on the users smartphone. This notification may be a combination of any of the above mentioned methods. When the dispensing event time window has been initiated, the dispensing button is disengaged and a countdown clock begins and is displayed on the smartphone app. This allows the patient to see how much time is remaining prior to the re-engagement of the dispensing button. This feature has been created to assist parents and caregivers to both monitor and ensure children do not exceed dosing quantities and helps reinforce the treatment regimen. There may be an app feature allowing the patient to extend the dispensing time window or reschedule the dispensing event to a time that is more convenient. The same mechanical feature that engages the dispensing button, can also engage the lower housing assembly to prevent removal. The lower housing may have a feature that extends up into the main housing when installed. This extended detail, or tab, allows the mechanical feature to engage the tab and prevent the lower assembly from being removed from the main housing. When the canister contents are depleted, the smart inhaler will disengage the tab and allow the user to remove the lower assembly.

During the examination of a patient, a physician determines that MMJ is a suitable alternative to addressing the patients ailments caused by Crohn's disease. The physician recommends the smart inhaler as the method of delivery for the MMJ. The physician logs into the online system network to access his assigned dashboard. The physician can browse various categories of information. One category may be "Patient Ailments", where numerous ailments are listed, such as but not limited to: ADHD, Alzheimer's, Arthritis, Cancer, Crohn's Disease, etc. The physician selects "Crohn's Disease" and a page of medicines specifically formulated for Crohn's is displayed. With each individual formulation listed, detailed information may be displayed such as but not limited to: Manufacturer/Formulator of Record, formulation contents, percentages and types of cannabinoids and THC, last date of formulation revision, etc. . . . . . Also displayed with each individual formulation is patient group feedback for that specific formulator's medicine. This data may be used by the physician is guiding his decision on which formulation to recommend. The group sourced feedback may provide information on formulation effectiveness, side effects, dispensing levels and dispensing frequency, likes/dislikes, etc. Patients may also have the ability to rate formulations on a scale of 1 to 5 to assist in establishing a method for "scoring" how successful formulators are at addressing ailments with their medicines. This scoring will allow physicians to quickly see which formulator is focused on providing the best results with their specific medicines. For example, the physician has 6 formulator's to select from with regards to medication for Crohn's disease. 4 of the six formulator's have a rating of less than 3 stars, 1 has a 3.4 stars and the remaining 2 have scores above 4 stars. The doctor can select the 2 highest ranked formulators and do a side by side product comparison, read patient feedback, and now make an educated decision on which formulator's medicine is best for his patient's specific ailment. The physician selects "Formulator #6" and a list of local dispensaries carrying that specific medicine is displayed allowing the physician to select a dispensary that is convenient for the patient. Next, a window may be displayed for the physician to enter the recommended dispensing regime for his patient. Information such as but not limited to, medicine dispensing amounts, dispensing frequency, treatment duration, approved refills, etc. will be entered and stored into the on-line system. When the prescription is entered, a unique ID code is generated and attached to an electronic prescription that is emailed to the patient or authorized guardian. The patient visits the dispensary and presents the e-prescription to be filled. The patient purchases the dispensing device and the prescription.

In order to use the dispensing device, the patient is first required to download and install the free smartphone application from Google Play® or the Apple Store® and the device's batteries must be fully charged. Once this is completed, the smartphone's Bluetooth wireless communication interface must be turned on. Bluetooth will search and detect the device and connect. The patient will open the device application and will be asked to complete some basic information, such as but not limited to: name, address, age, weight, etc. The patient will also be required to read and agree a "private information disclosure" that will allow for specific personal information to be gathered and synthesized from a HIPPA compliant database on the system network. Additional syncing of third party device collection methods such as Fitbit, Apple Watch etc. can be completed at this time. After this is completed, a "Device Manual and Patient Instruction" section will walk the patient through the device features and functions, how to use the device, how to install the MDI cartridge, how to dispense the medicine, FAQ's, troubleshooting, etc. Next, the patient will install the MDI canister. The app will instruct the user to place the MDI cartridge into the bottom of the main housing and slide up until the canister assembly locks into place. When the canister is being installed the device will detect this action and via the smartphone, prompt the user to enter the unique ID code that was included with their electronic prescription. When the code is entered, the system software will download the treatment regime recommended by the physician to the smartphone and then wirelessly transfer and flash this information to the device's memory. For example, the physician's recommendation is for the patient to dispense 6 mg or medicine every 4 hours. The device is now programmed to monitor, track and notify the patient for content dispensing according to the physician's recommendation. Also, when the canister is installed the device will wirelessly read the data stored on the canister assembly regarding the formulator of record, contents, date manufactured, etc. This information is uploaded in real-time to the on-line system network and is accessible by the physician and formulators. The device is ready for use and may remain disengaged until the first dispensing event is recorded. When the patient administers their first dispensing from a new canister, the device's internal clock starts and will notify the patient when the next dispensing event is required in 4 hours. For patient reference, a daily dispensing schedule may be displayed on the smartphone outlining the times throughout the day that a dispensing event should occur. After the initial dispensing of the new canister is complete, the device will engage the dispensing button preventing additional or accidental dispensing until the next scheduled dispensing event. The device will go into a sleep mode until the next dispensing event is approaching and at this time, the device will wake-up and vibrate and/or flash the LED indicator to notify the patient. The smartphone app can also simultaneously notify the patient through an audible alarm, vibration and/or screen message. The app will allow the patient to determine a window of time that the dispensing event can occur. This time can be adjusted and set for 15 to 30 minutes before and after the designated time. When a dispensing event is authorized and the time to dispense is within the set window of time, the device will continually send periodic reminders to the patient that the dispensing event needs to occur. A countdown timer may be displayed on the smartphone with the remaining time before the dispensing event window has expired. If the patient is in an inconvenience location, for example a client meeting at work, the patient may postpone the dispensing event for a future time prior to the next scheduled dispensing event. During an active dispensing event time window, the device's dispensing button will stay engaged and the device's LED indicator will flash green until the patient shakes the device and canister 5 or more times to mix the canister contents. The device's internal accelerometer detects this action and the LED indicator will change to a solid green and the dispensing button will disengage allowing the patient to press down the button and dispense the medicine. After the dispensing event has occurred the button is engaged and the device returns to a sleep mode. At any time between dispensing events, the patient can shake the device to force an exit from the sleep mode. After each dispensing event, the app will prompt the patient to answer a set of questions relating to the effects of the medicine. The patient will input their feedback and this information will be uploaded to the on-line system network in real-time for review by the physician and/or the formulator. This direct patient feedback is beneficial to the physician to ensure the prescribed regime is providing benefit to the patient and also allows the physician to monitor any negative side effects experienced by the patient. The formulator can also analyze the patient feedback to better understand the efficacy of the medicine they produce. This patient feedback can be used by the formulator to make adjustments to specific medicine chemistry. For example, a high number of Crohn's disease patients may be using a formulation to address their symptoms but 2 hours after a dispensing event, the pain has returned, they are experiencing sleepiness by midday and their anxiety levels are increasing. The formulator can then make necessary adjustments to address and/or eliminate these side effects and improve the effectiveness of this specific formulation for Crohn's patients. The device will track the total number of dispensing events for each individual canister. For example, a canister with a Crohn's disease formulation has incurred 60 dispensing events and is removed from the device and a new, nighttime formulation to help a patient sleep is inserted and incurs 2 dispensing events. The next morning, the patient removes the nighttime formulation and reinserts the Crohn's formulation, the device will count the next dispensing as event #61. The onboard memory located in the lower assembly (mouthpiece and canister) allows the device to recognize and track each individual formulation that is inserted/removed from the device. When a canister's contents have been depleted, the app will notify the user to remove the lower assembly and install a new canister.

An additional example of the device system in use could be for patient suffering from PTSD. Shortly prior to the time of dispensing the medicine at a scheduled time, the device system will instruct the patient to ensure their ancillary monitoring device, such as a FitBit, is on the patient's wrist. The system device may instruct and notify the user to initiate a blood pressure check at a specific time, for example, 5 minutes prior to the scheduled dosing time. The blood pressure device may be bluetooth enabled and the device system will automatically import the test results or the user may manually enter the results into the smartphone app of the smart inhaler system. The device system may also instruct the user to connect an ancillary blood oxygen monitor to their smartphone and clip the monitor to their finger tip 2-3 minutes before the dosing event. All of the data is captured prior to the dosing event and stored on the device system. The patient is then instructed to dispense the medicine. At specific time intervals following the dosing event, patient vitals and data will be monitored, automatically or manually entered and recorded by the device system. For example, the patient has a schedule doing event for 2:00 p.m., the device system sends a notification alert at 1:50 p.m. for the user to ensure their FitBit is charged and is on their wrist. The device system will instruct the user to sit, rest and refrain from any activity so that a resting heart rate can be obtained. Upon user confirmation, the device system begins to record the user's heart rate via input from the FitBit. At 1:55 p.m. the device system will instruct the user to take a blood pressure reading. The blood pressure test is performed and the system device will import the results from a Bluetooth enable blood pressure monitor or the user can manually input the results into the device system app, for example, 135/90 is typed and entered by the user into the device system's smartphone app. The device system may then send a notification to the user at 1:59 p.m. to connect an ancillary blood oxygen monitor an place the monitor's clip on the user's index finger. Now the device system has gathered and is continuously recording patient vitals prior to dosing. At 2:00 p.m. the device system notifies the patient it is time to dose their medication as prescribed by the physician. The patient dispenses the medication and the event is recorded by the device system and the post-dosing monitoring software program is initiated. The system device will continue to record vitals at specific time intervals. For example, the heart rate data is captured and recorded every 30 seconds for minutes 1-5 after dosing and then the device system captures and records the heart rate every 60 seconds for minutes 6-15. The system device may then instruct the user to take and enter a second blood pressure reading at the 5 minute mark after dosing and again at the 15 minute post-dosing mark. The blood oxygen monitoring may occur in a similar fashion as the heart rate monitoring and at specific time intervals, the readings will be captured and recorded in the device system. The post-dosing monitoring may only occur for the first 15 minutes after the dosing event or, depending on the patient's needs as determined by the physician, the post-dosing monitoring could may need to continue for the first 30 minutes after patient dosing and then for 15 minutes every hour until the next scheduled dosing event. The device system now has multiple patient data points to compare, analyze and categorize. The post-dosing patient monitoring period and the time in-between monitoring cycles is customizable according to the patient's medical needs. The patient monitoring system intervals may be provided in a device system default configuration, or be determined and adjusted by the physician, or automatically adjusted by AI analyzing patient vitals history and making recommendations based on patient treatment progress. Through the combination of using the smart inhaler, ancillary vital monitoring devices, capturing and recording patient vitals (pre and post-dosing) and using AI for predictive modeling, physicians and medicine formulators can make huge strides in improving individual treatment plans for patients and patient groups suffering from similar ailments.

The present disclosure may be implemented using a smart metered-dose inhaler that operated in concert with apps running on one or more mobile communication devices (e.g., smartphones) one or more network-based or cloud-based platforms. Each of these devices includes a controller utilizing a general purpose computing device, such as a microprocessor controlled by specialized computer software. As such, embodiments of the disclosure may comprise adapting or reconfiguring presently existing equipment. Alternatively, original equipment may be provided embodying the disclosure.

All of the methods described in this disclosure may include storing non-transient computer-executable instructions and associated results in a non-transient storage medium. These computer-executable instructions and results may include any of the computer-implemented procedures or results described in this disclosure and may be stored in any manner known in the art. The storage medium may include any storage medium described in this disclosure or any other suitable storage medium known in the art. After the computer-executable instructions or results have been stored, they can be accessed in the storage medium and used by any of the method or system embodiments described in this disclosure, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Those having skill in the art will appreciate that there are various vehicles by which processes and/or systems and/or other technologies described in this disclosure can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described in this disclosure may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth in this disclosure, and then use engineering practices to integrate such described devices and/or processes into data processing systems. That is, at least a portion of the devices and/or processes described can be integrated into a data processing system via a reasonable amount of experimentation. Those having skill in the art will recognize that a typical data processing system generally comprises one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems. All of the technology described in this disclosure is suitable for implementation using commercially available computing devices, such as microprocessors executing computer-executable software. These computing devices may be interconnected via the Internet, mobile telephone voice and data system, or other data suitable network.

This disclosure sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components may be combined to achieve a particular functionality can be seen as "associated with" each other such that the desired functionality is achieved, irrespective of architectures or intermediate components. Likewise, any two components so associated can also be viewed as being "connected", or "coupled", to each other to achieve the desired functionality, and any two components capable of being so associated can also be viewed as being "functionally connected" to each other to achieve the desired functionality. Specific examples of functional connection include but are not limited to physical connections and/or physically interacting components and/or wirelessly communicating and/or wirelessly interacting components and/or logically interacting and/or logically interacting components.

While particular aspects of the present subject matter have been shown and described in detail, it will be apparent to those skilled in the art that, based upon the teachings of this disclosure, changes and modifications may be made without departing from the subject matter described in this disclosure and its broader aspects and, therefore, the appended claims are to encompass within their scope all such changes and modifications as are within the true spirit and scope of the subject matter described in this disclosure. Although particular embodiments of this disclosure have been illustrated, it is apparent that various modifications and embodiments of the disclosure may be made by those skilled in the art without departing from the scope and spirit of the disclosure.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. The disclosure is defined by the following claims, which should be construed to encompass one or more structures or function of one or more of the illustrative embodiments described above, equivalents and obvious variations. it will therefore be appreciated that present invention provides significant improvements in electric power circuit reclosers. The foregoing relates only to the exemplary embodiments of the present invention, and that numerous changes may be made therein without departing from the spirit and scope of the invention as defined by the following claims.

The invention claimed is:

1. An electronic metered-dose inhaler system including security features comprising a cartridge, a pump unit, and a mobile app, wherein:
   the cartridge comprises:
      a canister containing pressurized contents for aerosol dispensing without burning or vaporizing the contents of the canister,
      an electronically readable cartridge memory storing security information comprising canister contents information about the contents of the canister,
      a mouthpiece unit holding the canister against a spring biasing the canister in a retraction direction allowing the canister to be reciprocated between the retraction direction and an opposing insertion direction to dispense a portion of the contents of the canister through the mouthpiece unit each time the canister is reciprocated,
      wherein the mouthpiece unit further comprises a reusable clip for removably attaching the cartridge to the pump unit in an operational configuration with the canister positioned for reciprocation by the pump unit;
   the pump unit comprises:
      a pump actuator positioned to reciprocate the canister to dispense the contents of the canister through the mouthpiece unit when the cartridge is attached to the pump unit in the operational configuration;

a battery powering a microprocessor, a memory, a wireless radio, and a cartridge memory reader operative for reading the cartridge memory to obtain the security information when the cartridge is attached to the pump unit in the operational configuration;

wherein the memory is operative for storing the security information and associated security procedures;

wherein the microprocessor is operative for unlocking the pump actuator to allow operation of the pump actuator in accordance with the security procedures and security information, and for locking the pump actuator to prevent operation of the pump actuator that is not in accordance with the security procedures and security information;

wherein the mobile app is associated with an authorized user, configured to run on a mobile device configured to pair and communicate with the microprocessor of the pump unit, and wherein the mobile app is configured to execute computer instructions comprising:

receiving additional security information from a cloud-based system over a network comprising an authorized aerosol product, an authorized consumer of the aerosol product, and an authorized dosing protocol for the aerosol product, downloading the additional security information to the pump unit over a wireless link with the wireless radio of the pump unit, causing the authorized user's mobile device to display security notifications in accordance with the additional security information, causing the pump unit to unlock for dispensing the contents of the canister in accordance with the authorized dosing protocol when the authorized consumer of the aerosol product received by the mobile app over the network matches the authorized user of the mobile app, and when the authorized aerosol product received by the mobile app over the network matches the canister contents information read by the pump unit the cartridge memory, wherein the mouthpiece unit further comprises a single-use clasp disposed on an inner surface of the mouthpiece unit extending inward and in the insertion direction from the inner surface of the mouthpiece unit allowing the canister to be inserted into the mouthpiece unit in the insertion direction, constraining the canister in the mouthpiece unit for reciprocation, and breaking away to disable the mouthpiece unit when the canister is removed from the mouthpiece unit in the retraction direction.

2. The electronic metered-dose inhaler system of claim 1, wherein:

the microprocessor is operative for unlocking the pump actuator to allow operation of the pump actuator in accordance with the authorized dosing protocol, and for locking the pump actuator to prevent operation of the pump actuator that is not in accordance with the authorized dosing protocol;

the mobile app is configured to execute computer instructions further comprising displaying the authorized dosing protocol, and causing the authorized user's mobile device to display dosing notifications in accordance with the authorized dosing protocol.

3. The electronic metered-dose inhaler system of claim 1, wherein the mobile app is further configured to execute computer instructions comprising:

determining a lock-out status for the canister;

downloading a lock-out notification to the pump unit causing the pump unit to disable dispensing the contents of the canister.

4. The electronic metered-dose inhaler system of claim 3, wherein the additional security information comprises a prescription downloaded from a provider system over the network identifying a medication and an authorized patient, and wherein the mobile app is further configured to execute computer instructions comprising:

uploading the security information describing the contents of the canister from the pump unit;

determining the lock-out status in response to determining that the medication identified by the prescription does correspond to the medication in the canister.

5. The electronic metered-dose inhaler system of claim 3, wherein the additional security information comprises a prescription downloaded from a provider system over the network identifying a medication and an authorized patient, and wherein the mobile app is further configured to execute computer instructions comprising:

receiving user identification for the authorized user through the mobile device;

determining the lock-out status in response to determining that the authorized patient identified by the prescription does not correspond to the authorized user associated with the user identification.

6. The electronic metered-dose inhaler system of claim 3, wherein the mobile app is further configured to execute computer instructions comprising:

displaying one or more lock-out notifications on the authorized user's mobile device uploading a lock-out status to a provider system.

7. An electronic metered-dose inhaler including security features comprising a cartridge and a pump unit, wherein:

the cartridge comprises:

a canister containing pressurized contents for aerosol dispensing without burning or vaporizing the contents of the canister, an electronically readable cartridge memory storing security information comprising contents information about the contents of the canister, a mouthpiece unit holding the canister against a spring biasing the canister in a retraction direction allowing the canister to be reciprocated between the retraction direction and an opposing insertion direction to dispense a portion of the contents of the canister through the mouthpiece unit each time the canister is reciprocated, wherein the mouthpiece unit further comprises a reusable clip for removably attaching the cartridge to the pump unit in an operational configuration with the canister positioned for reciprocation by the pump unit, wherein the cartridge memory is positioned so that the security information is readable by a cartridge memory reader carried by the pump unit when the cartridge is attached to the pump unit in the operable configuration;

the pump unit comprises:

a pump actuator positioned to reciprocate the canister to dispense the contents of the canister through the mouthpiece unit when the cartridge is attached to the pump unit in the operational configuration;

a battery powering a microprocessor, a memory, and a cartridge memory reader operative for reading the cartridge memory to obtain the security information when the cartridge is attached to the pump unit in the operational configuration;

wherein the memory is operative for storing the security information and associated security procedures;

wherein the microprocessor is operative for unlocking the pump actuator to allow operation of the pump actuator in accordance with the security procedures and security information, and for locking the pump actuator to prevent operation of the pump actuator that is not in accordance with the security procedures and security information;

wherein the pump unit further comprises a wireless radio powered by the battery operative for wirelessly receiving the security information;

wherein the microprocessor is operative for wirelessly receiving a stop-use notification relating to the cartridge and preventing the pump unit from further dispensing the contents of the canister in accordance with the stop-use notification, wherein the mouthpiece unit further comprises a single-use clasp disposed on an inner surface of the mouthpiece unit extending inward and in the insertion direction from the inner surface of the mouthpiece unit allowing the canister to be inserted into the mouthpiece unit in the insertion direction, constraining the canister in the mouthpiece unit for reciprocation, and breaking away to disable the mouthpiece unit when the canister is removed from the mouthpiece unit in the retraction direction.

8. The electronic metered-dose inhaler of claim 7, wherein the stop-use notification is associated with a recall of the contents of the canister, expiration of the canister, prescription termination, or clinical trial termination.

9. The electronic metered-dose inhaler of claim 7, wherein:
the pump unit further comprises an accelerometer powered by the battery;
the security information further comprises a shaking protocol;
the microprocessor is configured to determined when the inhaler has been adequately shaken based on information from the accelerometer and the shaking protocol;
the microprocessor is operative for unlocking the pump actuator to allow operation of the pump actuator in response to determining that the inhaler has been adequately shaken, and for locking the pump actuator to prevent operation of the pump actuator in response to determining that the inhaler has not been adequately shaken.

10. The electronic metered-dose inhaler of claim 7, wherein the pump actuator comprises a dispensing button configured for manual operation by a user.

11. The electronic metered-dose inhaler of claim 10, wherein the microprocessor is operative to lock the pump actuator by causing an abutment to move to block movement of the dispensing button, and operative to unlock the pump actuator by causing the abutment to move to unblock movement of the dispensing button.

12. The electronic metered-dose inhaler of claim 7, wherein the pump unit further comprises an LED powered by the battery and controlled by the microprocessor to display notifications in accordance with the security information.

13. The electronic metered-dose inhaler of claim 7, wherein the cartridge memory reader is selected from the group consisting of a barcode reader, an RFID reader and an NFC chip reader.

14. A cartridge including security features for an electronic metered-dose inhaler, comprising:
a canister containing pressurized contents for aerosol dispensing without burning or vaporizing the contents of the canister;
an electronically readable cartridge memory carried by the cartridge storing security information comprising contents information about the contents of the canister;
a mouthpiece unit holding the canister against a spring biasing the canister in a retraction direction allowing the canister to be reciprocated between the retraction direction and an opposing insertion direction to dispense a portion of the contents of the canister through the mouthpiece unit each time the canister is reciprocated;
wherein the mouthpiece unit further comprises a reusable clip for removably attaching the cartridge to a pump unit of the inhaler in an operational configuration with the canister positioned for reciprocation by the pump unit;
wherein the cartridge memory is positioned so that the security information is readable by a cartridge memory reader carried by the pump unit when the reusable clip attaches the cartridge to the pump unit in the operable configuration;
wherein the mouthpiece unit further comprises a single-use clasp disposed on an inner surface of the mouthpiece unit extending inward and in the insertion direction from the inner surface of the mouthpiece unit allowing the canister to be inserted into the mouthpiece unit in the insertion direction, constraining the canister in the mouthpiece unit for reciprocation, and breaking away to disable the mouthpiece unit when the canister is removed from the mouthpiece unit in the retraction direction.

15. The cartridge of claim 14, wherein the security information identifies a medication in the canister.

16. The cartridge of claim 14, wherein the single-use clasp comprises a pair of opposing flanges extending inward and in the insertion direction from the inner surface of the mouthpiece unit.

17. The cartridge of claim 14, wherein the cartridge memory is selected from the group consisting of a barcode, an RFID tag, and an NFC chip.

18. The cartridge of claim 14, wherein the canister comprises a valve stem and movement of the canister in the insertion direction pushes the valve stem into the mouthpiece unit to dispense a portion of the contents through the mouthpiece unit.

19. The cartridge of claim 14, wherein the canister contents comprise a pressurized medically-safe inhalant.

20. The cartridge of claim 14, wherein the canister contains contents selected from the group consisting of a medical marijuana product, nicotine, a pain killer, sleep aids, a dietary stimulant, and a dietary suppressant.

* * * * *